(12) United States Patent
Murphy et al.

(10) Patent No.: US 7,951,577 B2
(45) Date of Patent: *May 31, 2011

(54) LIQUID CRYSTALS WITH REDUCED TOXICITY AND APPLICATIONS THEREOF

(75) Inventors: Christopher John Murphy, Madison, WI (US); Nicholas L. Abbott, Madison, WI (US); Yan-Yeung Luk, Manlius, NY (US); Sean Francis Campbell, Bothell, WA (US); Li-Lin Cheng, Madison, WI (US); Chang-Hyun Jang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 784 days.

This patent is subject to a terminal disclaimer.

(21) Appl. No.: 11/877,029

(22) Filed: Oct. 23, 2007

(65) Prior Publication Data

US 2008/0050799 A1 Feb. 28, 2008

Related U.S. Application Data

(62) Division of application No. 10/892,827, filed on Jul. 16, 2004, now Pat. No. 7,303,694.

(60) Provisional application No. 60/488,065, filed on Jul. 17, 2003.

(51) Int. Cl.
| | |
|---|---|
| *C12N 5/00* | (2006.01) |
| *C09K 19/54* | (2006.01) |
| *C09K 19/30* | (2006.01) |
| *C09K 19/36* | (2006.01) |

(52) U.S. Cl. .............. 435/243; 435/404; 252/299.5; 252/299.63; 252/299.7

(58) Field of Classification Search ............. 252/299.01, 252/299.63, 299.5, 299.7; 435/243, 404
See application file for complete search history.

(56) References Cited

U.S. PATENT DOCUMENTS

| | | | |
|---|---|---|---|
| 4,597,942 | A | 7/1986 | Meathrel |
| 4,628,037 | A | 12/1986 | Chagnon et al. |
| 4,725,669 | A | 2/1988 | Essex et al. |
| 4,812,556 | A | 3/1989 | Vahlne et al. |
| 4,941,992 | A | 7/1990 | Jackson et al. |

(Continued)

FOREIGN PATENT DOCUMENTS

DE 3617710 A1 12/1986

(Continued)

OTHER PUBLICATIONS

Skaife, J. J. et al., "Influence of Nanometer-Scale Topography of Surfaces on the Orientational Response of Liquid Crystals to Proteins Specifically Bound to Surface-Immobilized Receptors," *Langmuir*, vol. 17, No. 18, pp. 5448-5457, 2001; American Chemical Society (Washington, D.C.).

(Continued)

*Primary Examiner* — Shean C Wu
(74) *Attorney, Agent, or Firm* — Foley & Lardner LLP

(57) ABSTRACT

Liquid crystal compositions that exhibit little or no toxicity with respect to cells include liquid crystals with chemical functional groups such as fluorine atoms, fluorophenyl groups, or difluorophenyl groups. Liquid crystals with little or no toxicity to cell lines may be added to cell culture media or added to components used in cell culture media. Cells may be grown in cell culture media that includes liquid crystals that exhibit little or no toxicity to cells.

17 Claims, 29 Drawing Sheets

U.S. PATENT DOCUMENTS

| | | | |
|---|---|---|---|
| 5,091,318 | A | 2/1992 | Anawis et al. |
| 5,568,256 | A | 10/1996 | Körner et al. |
| 5,620,850 | A | 4/1997 | Bamdad et al. |
| 5,686,018 | A | 11/1997 | Demus et al. |
| 5,712,103 | A | 1/1998 | Leavitt et al. |
| 5,940,201 | A | 8/1999 | Ash et al. |
| 5,985,171 | A | 11/1999 | Rieger et al. |
| 6,005,668 | A | 12/1999 | Held, III et al. |
| 6,060,327 | A | 5/2000 | Keen |
| 6,097,484 | A | 8/2000 | McIntosh et al. |
| 6,159,681 | A | 12/2000 | Zebala |
| 6,168,839 | B1 | 1/2001 | Fujita et al. |
| 6,171,802 | B1 | 1/2001 | Woolverton et al. |
| 6,178,034 | B1 | 1/2001 | Allemand et al. |
| 6,203,304 | B1 | 3/2001 | Lopez Tonazzi et al. |
| 6,207,369 | B1 | 3/2001 | Wohlstadter et al. |
| 6,277,489 | B1 | 8/2001 | Abbott et al. |
| 6,284,197 | B1 | 9/2001 | Abbott et al. |
| 6,288,392 | B1 | 9/2001 | Abbott et al. |
| 6,291,188 | B1 | 9/2001 | Meade et al. |
| 6,306,594 | B1 | 10/2001 | Cozzette et al. |
| 6,383,815 | B1 | 5/2002 | Potyrailo |
| 6,383,816 | B1 | 5/2002 | Wirth et al. |
| 6,413,587 | B1 | 7/2002 | Hawker et al. |
| 6,491,061 | B1 | 12/2002 | Lopez et al. |
| 6,540,939 | B1 | 4/2003 | Martin et al. |
| 6,692,699 | B2 | 2/2004 | Abbott et al. |
| 6,797,463 | B2 | 9/2004 | Abbott et al. |
| 6,824,837 | B2 | 11/2004 | Abbott et al. |
| 7,303,694 | B2 * | 12/2007 | Murphy et al. .......... 252/299.01 |
| 2002/0004216 | A1 | 1/2002 | Abbott et al. |
| 2002/0025391 | A1 | 2/2002 | Angelopoulos et al. |
| 2002/0028451 | A1 | 3/2002 | Abbott et al. |
| 2002/0055093 | A1 | 5/2002 | Abbott et al. |
| 2002/0071943 | A1 | 6/2002 | Hawker et al. |
| 2002/0142453 | A1 | 10/2002 | Abbott et al. |
| 2002/0164604 | A1 | 11/2002 | Abbott et al. |
| 2003/0071949 | A1 | 4/2003 | Abbott et al. |
| 2003/0099993 | A1 | 5/2003 | Abbott et al. |
| 2003/0180966 | A1 | 9/2003 | Abbott et al. |
| 2003/0194753 | A1 | 10/2003 | Abbott et al. |
| 2004/0091620 | A1 | 5/2004 | Abbott et al. |

FOREIGN PATENT DOCUMENTS

| | | |
|---|---|---|
| EP | 0 284 587 | 8/1988 |
| EP | 0 345 462 | 12/1989 |
| JP | 02-311822 A2 | 12/1990 |
| JP | 02-311824 A2 | 12/1990 |
| JP | 03-010222 A2 | 1/1991 |
| JP | 03-039932 A2 | 2/1991 |
| JP | 04-057024 A2 | 2/1992 |
| JP | 04-057025 A2 | 2/1992 |
| JP | 04-284423 A2 | 10/1992 |
| JP | 05-134257 A2 | 5/1993 |
| JP | 05-134258 A2 | 5/1993 |
| JP | 06-175136 A2 | 6/1994 |
| JP | 06-194513 A2 | 7/1994 |
| JP | 06-194662 A2 | 7/1994 |
| WO | WO 92/08978 | 5/1992 |
| WO | WO 99/63329 | 12/1999 |
| WO | WO 99/64862 | 12/1999 |
| WO | WO 01/61325 | 8/2001 |
| WO | WO 01/61357 | 8/2001 |

OTHER PUBLICATIONS

Abbott, N. L., "Biophotonics based on Liquid Crystals: Development of New Principles Suitable for Profiling of Regulatory Signaling Proteins," Oral Presentation at LEOS Annual Meeting, Nov. 12, 2001, San Diego, California.

Luk, Y.-Y. et al., "Using Liquid Crystals and Nanostructured Surfaces to Assay for Regulatory Proteins Involved in Cell Signaling Pathways," Abstract No. 199 for presentation at 76th Colloid and Surface Science Symposium, Jun. 23-26, 2002, University of Michigan, Ann Arbor, Michigan.

Sheppard, B.C. et al., "Effects of Paclitaxel on the Growth of Normal, Polyposis, and Cancerous Human Colonic Epithelial Cells," *Cancer*, vol. 85, pp. 1454-1464, 1999; American Cancer Society.

Luk, Y.-Y. et al., "Using Liquid Crystals to Amplify Protein-Receptor Interactions: Design of Surfaces with Nanometer-Scale Topography that Present Histidine-Tagged Protein Receptors," *Langmuir*, vol. 19, pp. 1671-1680, 2003; American Chemical Society.

Kim, S. R. et al., "Manipulation of the Orientational Response of Liquid Crystals to Proteins specifically Boundn to Covalently Immobilized and Mechanically Sheared Films of Functionalized Bovine Serum Albumin," *Langmuir*, vol. 18, pp. 5269-5276, 2002; American Chemical Society.

Kim, S. R. et al., "Rubbed Films of Functionalized Bovin Serum Albumin as Substrates for the Imaging of Protein-Receptor Interactions Using Liquid Crystals," *Adv. Mater.*, vol. 13, pp. 1445-1449, 2001; Wiley-VCH Verlag GmbH (Weinheim).

Shah, R, R. et al., "Principles for Measurement of Chemical Exposure Based on Recognition-Driven Anchoring Transitions in Liquid Crystals," *Science*, vol. 293, pp. 1296-1299, Aug. 17, 2001; American Association for the Advancement of Science (Washington D.C.).

Kapur, T. et al., "Streamlining the Drug Discovery Process by Integrating Miniaturization, High Throughput Screening, High Content Screening, and Automation on the CellChip™ System," *Biomed. Microdevices*, vol. 2, pp. 99-109, 1999; Kluwer Academic Publishers (Boston).

Straub, B. et al., "Recombinant maxi-K channels on transistor, a prototype of iono-electronic interfacing," *Nat. Biotechnol.*, vol. 19, pp. 121-124, 2001; Nature Publishing Group.

Gooby, J. W., "Liquid crystals and life," *Liquid Crystals*, vol. 24, pp. 25-38, 1998; Taylor & Francis Ltd.

Fang, J. et al., "Imaging Biological Cells Using Liquid Crystals," *Langmuir*, vol. 19, pp. 2865-2869, 2003; American Chemical Society.

Takatsu, H. et al., "Investigation activity and data on the safety of liquid crystal materials," *Mol. Cryst. and Liq. Cryst.*, vol. 364, pp. 171-186, 2001; Overseas Publishers Assoc. N.V.

Cognard, J. "Alignment of Nematic Liquid Crystals and Their Mixtures," *Mol. Cryst. Liq. Cryst. Suppl. Ser.*, vol. 1, pp. 1-75, 1982; Gordon and Breach Science Publishers (New York).

Kirsch, P. et al., "Nematic Liquid Crystals for Active Matrix Displays: Molecular Design and Synthesis," *Agnew. Chem. Int. Ed.*, vol. 39, pp. 4216-4235, 2000; Wiley-VCH Verlag GmbH (Weinheim).

Dingemans, T. J. et al., "Javelin-, Hockey Stick-, and Boomerang-Shaped Liquid Crystals. Structural Variations on *p*-Quinquephenyl," *J. Phys. Chem. B*, vol. 105, pp. 8845-8860, 2001; American Chemical Society.

Petrzilka, M., "Apolar Acetylenic Liquid Crystals," *Mol. Cryst. Liq. Cryst.*, vol. 111, pp. 347-138, 1984; Gordon and Breach Science Publishers, Inc.

Qian, X. M. et al., "Study on Synthesis and Properties of *p*-Alkylcyclohexylethane Series Liquid Crystals," *Journal of East China University of Science and Technology*, vol. 20, pp. 688-692, 1994; Tsinghua Tongfang Optical Disc Co., Ltd. (1995-2005). (English language abstract included.).

Chen, C. S. et al., "Geometric Control of Cell Life and Death," *Science*, vol. 276, pp. 1425-1428, 1997.

Luk, Y.-Y. et al., "Self-Assembled Monolayers of Alkanethiolates Presenting Mannitol Groups Are Inert to Protein Adsorption and Cell Attachment," *Langmuir*, vol. 16, pp. 9604-9608, 2000; American Chemical Society.

Miranti, C. et al., "Sensing the environment: a historical perspective on integrin signal transduction," *Nat. Cell Biol.*, vol. 4, pp. 83-90, 2002; Macmillan Magazines Ltd.

Danen, E. H. J. et al., "Fibronectin, Integrins, and Growth Control," *J. Cell Physiol.*, vol. 189, pp. 1-13, 2001; Wiley-Liss, Inc.

Guittard, F. et al., "Highly fluorinated thermotropic liquid crystals: an update," *J. Fluorine Chem.*, vol. 100, pp. 85-96, 1999; Elsevier Science S.A.

Ma, J. C. et al., "The Cation-$\pi$ Interaction," *Chem. Rev.*, vol. 97, pp. 1303-1324, 1997; American Chemical Society.

Dougherty, D. A., "Cation-$\pi$ Interactions in Chemistry and Biology: A New View of Benzene, Phe, Tyr, and Trp," *Science*, vol. 271, pp. 163-168, 1996.

Mecozzi, S. et al., "Cation-π interactions in aromatics of biological and medicinal interest: Electrostatis potential surfaces as a useful qualitative guide," *Natl. Acad. Sci. USA*, vol. 93, pp. 10566-10571, 1996.

West, A. P. et al., "Theoretical Studies of the Supramolecular synthon Benzene . . . Hexafluorobenzene," *J. Phys. Org. Chem.*, vol. 10, pp. 347-350, 1997; John Wiley & Sons, Ltd.

Waters, M. L., "Aromatic interactions in model systems," *Curr. Opin. Chem. Biol.*, vol. 6, pp. 736-741, 2002; Elsevier Science Ltd.

Weck, M. et al., "Influence of Perfluoroarene—Arene Interactions on the Phase Behavior of Liquid Crystalline and Polymeric Materials," *Angew. Chem. Int. Ed.*, vol. 38, pp. 2741-2745, 1999; Wiley-VCH Verlag GmbH (Weinheim).

Hemmerling, T. M. "Desflurane reduces the effective therapeutic infusion rate (ETI) of cisatracurium more than isoflurane, sevoflurane, or propofol," *Can. J. Anaesth.*, vol. 48, pp. 532-537, 2001.

Teicher, B., "Use of Perfluorocarbon Emulsions in Cancer Therapy," *Blood Substitutes and Oxygen Carriers*, pp. 640-647, 1993, T. M. S. Chang (ed.); Marcel Dekker, New York.

Chia, S. et al., "Working Supramolecular Machines Trapped in Glass and Mounted on a Film Surface," *Angewandte Chemie-International Ed.*, vol. 40, p. 2447, 2001; Wiley-VCH Verlag GmgH (Weinheim).

Abbott, N. L. et al., "Orientations of liquid crystals on self-assembled monolayers formed from alkanethiols on gold," ACS Symposium Series, vol. 695, pp. 81-103, 1998.

Dunk, C. et al., "Vascular endothelial growth factor receptor-2-mediated mitogenesis is negatively regulated by vascular endothelial growth factor receptor-1 in tumor epithelial cells," *Am. J. Pathol.*, vol. 158, pp. 265-273, 2001; American Society for Investigative Pathology.

Gupta, V. K. et al., "Using Isotropic, Nematic and Smectic Fluids for the Study of Self-Assembled Monolayers Formed from Alkanethiols on Gold," *Chemistry of Materials*, vol. 8, pp. 1366-1369, 1996; American Chemical Society.

Gupta, V. K. et al., "Design of Surfaces for Patterned Alignment of Liquid Crystals on Planar and Curved Substrates," *Science*, vol. 276, pp. 1533-1536, 1997.

Miller, W. J. et al., "Comparison of the anchoring of nematic liquid crystals on self-assembled monolayers formed from semifluorinated thiols and alkanethiols," *Liquid Crystals*, vol. 23, pp. 175-184, 1997; Taylor & Francis Ltd.

Sheppard, B. C. et al., "Effects of Paclitaxel on the Growth of Normal, Polyposis, and Cancerous Human Colonic Epithelial Cells," *Cancer*, vol. 85, pp. 1454-1464, 1999; American Cancer Society.

Skaife, J. et al., "Quantitative Interpretation of the Optical Textures of Liquid Crystals Caused by Specific Binding of Immunoglobulins to Surface-Bound Antigens," *Langmuir*, vol. 16, pp. 3529-3536, 1999; American Chemical Society.

Ennulat, D. et al., "Thermal Radiography Utilizing Liquid Crystals," *Mol. Cryst. Liq. Cryst.*, vol. 13, pp. 149-164, 1971; Gordon and Breach Science Publishers (Great Britain).

"Liquid Crystals in Liquid Crystal Displays Last Update: Dec. 28, 2000 Statement of the German Federal Environmental Agency Concerning the Ecotoxicology of Liquid Crystals in Liquid Crystal Displays: Status Aug. 2000" from http://www.umweltbundesamt.de/uba-info-daten-e/daten-e/lcd.htm (English language) Umweltbundesamt.de. (Dessau, Germany).

Takeshi, I., "Chapter 12: Fluorinated Liquid Crystals," *Organofluorine Chemistry: Principles and Commercial Applications*, pp. 263-286, R. E. Banks et al. (eds.); Plenum Press, New York.

Cox, J.S.G., "Disodium Cromoglycate (FPL 670) (Intal'*); a Specific Inhibitor of Reaginic Antibody-Antigen Mechanisms," *Nature*, vol. 216, pp. 1328-1329 (1967), published by Nature Publishing Group (Washington, D.C.).

Novak, T. J. et al., "Use of Anisotropic Materials as Chemical Detectors," *Analytical Letters*, vol. 5, No. 3, pp. 187-192, 1972, published by Marcel Dekker, Inc. (New York, NY).

Poziomek, E. J. et al., "Use of Liquid Crystals as Vapor Detectors," *Mol. Cryst. Liq. Cryst.*, vol. 27, pp. 175-185, 1973, published by Gordon and Breach Science Publishers, Ltd., (Holland).

Saji, T. et al., "Reversible Formation and Disruption of Micelles by Control of the Redox State of the Head Group," *J. Am. Chem. Soc.*, vol. 107, pp. 6865-6868, 1985, published by the American Chemical Society (Washington, D.C.).

Heslot, F. et al., "Molecular Layering in the Spreading of Wetting Liquid Drops," *Nature*, vol. 338, pp. 640-642, 1989, published by Nature Publishing (New York, NY).

Pieranski P. et al., "Adsorption-Induced Anchoring Transitions at Nematic-Liquid-Crystal-Crystal Interfaces," *Phys. Rev. A.*, vol. 40, No. 1, pp. 317-322, Jul. 1, 1989, published by the American Physical Society (Washington D.C).

Starkey, C.A. et al. "Evaluation of the Recombigen HIV-1 Latex Agglutination Test," *J. Clin. Microbiol.*, vol. 28, No. 4, pp. 819-822, Apr. 1990, published by the American Society for Microbiology (Washington D.C.).

Parish et al., "A Polyanion Binding Site on the CD4 Molecule, Proximity to the HIV-gp120 Binding Region," *The Journal of Immunology*, vol. 145, No. 4, pp. 1188-1195, Aug. 15, 1990, published by the American Association of Immunologists, Inc. (Bethesda, MD).

Häussling, L. et al. "Biotin-Functionalized Self-Assembled Monolayers on Gold: Surface Plasmon Optical Studies of Specific Recognition Reactions," *Langmuir*, vol. 7, No. 9, pp. 1837-1840, Sep. 1991, published by the American Chemical Society (Washington, D.C.).

Jérôme, B., "Surface Effects and Anchoring in Liquid Crystals," *Rep. Prog. Phys*. vol. 54, pp. 391-452, 1991, published by IOP publishing Ltd. (United Kingdom).

Saji, T. et al., "Formation of Organic Thin Films by Electrolysis of Surfactants with the Ferrocenyl Moiety," *J. Am. Chem. Soc.*, vol. 113, pp. 450-456, 1991, published by the American Chemical Society (Washington, D.C.).

Schmitt, F.-J. et al., "Surface Plasmon Studies of Specific Recognition Reactions at Self-Assembled Monolayers on Gold," *Thin Solid Films*, vol. 210/211, pp. 815-817, 1992, published by Elsevier Sequoia.

Charych, D.H. et al., "Direct Colorimetric Detection of a Receptor-Ligand Interaction by a Polymerized Bilayer Assembly", *Science*, vol. 261, pp. 585-588, Jul. 30, 1993, published by the American Association for the Advancement of Science (Washington D.C.).

Cocchi, J.M. et al., "Comparison Between Direct Binding, Competition and Agglutination Assays in the Characterization of Polyclonal Anti-idiotypes Against Anti-HBs Human Monoclonal Antibodies," *Immunological Meth.*, vol. 160, pp. 1-9, 1993, Elsevier Science Publishers.

H. Weetall, "Preparation of Immobilized Proteins Covalently Coupled Through Silane Coupling Agents to Inorganic Supports," *Applied Biochemistry and Biotechnology*, vol. 41, pp. 157-188, 1993, published by Humana Press Inc. (Totowa, NJ).

Kuby, J., *Immunology*, Second Edition (1994), pp. 147-150, W.H. Freeman and Company (New York, NY).

Drawhorn, R. A. et al., "Anchoring of Nematic Liquid Crystals on Self-Assembled Monolayers Formed from Alkanethiols on Semitransparent Films of Gold," *J. Phys. Chem.*, vol. 99, No. 45, pp. 16511-16515, 1995, published by the American Chemical Society (Washington D.C.).

Gupta, V. K. et al., "Uniform Anchoring of Nematic Liquid Crystals on Self-Assembled Monolayers Formed from Alkanethiols on Obliquely Deposited Films of Gold," *Langmuir*, vol. 12, pp. 2587-2593, 1996; published by American Chemical Society (Washington D.C.).

Gupta, V. K. et al., "Azimuthal Anchoring Transition of Nematic Liquid Crystals on Self-Assembled Monolayers Formed from Odd and Even Alkanethiols," *Physical Review E*, vol. 54, No. 5, pp. R4540-R4543, Nov. 1996, published by The American Physical Society (Washington D.C.).

Yang, H. C. et al., "Molecular Interactions between Organized, Surface-Confined Monolayers and Vapor-Phase Probe Molecules. 8. Reactions between Acid-Terminated Self-Assembled Monolayers and Vapor-Phase Bases," *Langmuir*, vol. 12, pp. 726-735, 1996, published by American Chemical Society (Washington D.C.).

Gallardo, B. S. et al., "Ferrocenyl Surfactants at the Surface of Water: Principles for Active Control of Interfacial Properties," *Langmuir*, vol. 12, pp. 4116-4124, 1996, published by the American Chemical Society (Washington, D.C.).

Cornell, B.A. et al., "A Biosensor that uses Ion-Channel Switches," *Nature*, vol. 387, pp. 580-583, Jun. 5, 1997, published by Nature Publishing (New York, NY).

Lin, V. et al., "A Porous Silicon-Based Optical Interferometric Biosensor," *Science*, vol. 278, pp. 840-843, Oct. 31, 1997, published by the American Association for the Advancement of Science (Washington, D.C.).

Pan, J. J. et al., "Molecular Recognition and Colorimetric Detection of Cholera Toxin by Poly(diacetylene) Liposomes Incorporating Gm1 Ganglioside," *Langmuir*, vol. 13, No. 6, pp. 1365-1367, 1997, published by the American Chemical Society (Washington, D.C.).

Delamarche, E. et al., "Patterned Delivery of Immunoglobulins to Surfaces Using Microfluidic Networks," *Science*, vol. 276, pp. 779-781, May 2, 1997, published by the American Association for the Advancement of Science (Washington, D.C.).

Gupta, V. K. et al., "Optical Amplification of Ligand-Receptor Binding Using Liquid Crystals," *Science*, vol. 279, pp. 2077-2080, Mar. 27, 1998, published by the American Association for the Advancement of Science (Washington D.C.).

Ricco, A. J., "Surface Acoustic Wave Chemical Sensor Arrays: New Chemically Sensitive Interfaces Combined with Novel Cluster Analysis to Detect Volatile Organic Compounds and Mixtures," *Acc. Chem. Res.*, vol. 31, pp. 289-296, 1998, published by American Chemical Society (Washington D.C.).

Crooks, R. M. et al., "New Organic Materials Suitable for Use in Chemical Sensor Arrays," *Acc. Chem. Res.*, vol. 31, pp. 219-227, 1998, published by American Chemical Society (Washington D.C.).

Xia Y. N. et al., "Soft Lithography," *Angew. Chem. Int. Ed.*, vol. 37, pp. 551-575, 1998, published by Wiley Interscience (Germany).

Dancil, K. S. et al., "A Porous Silicon Optical Biosensor: Detection of Reversible Binding of IgG to a Protein A-Modified Surface," *J. Am. Chem. Soc.*, vol. 121 pp. 7925-7930, 1999, published by the American Chemical Society (Washington D.C.).

Naoka, M. et al., "Ferroelectric Liquid Crystal Alignment Films Utilizing Poly (DL amino acids) and Fibrous Proteins," *Kobunshi Ronbunshu*, vol. 56, No. 6, pp. 396-400, Jun. 1999.

Skaife, J. J. et al., "Quantitative Characterization of Obliquely Deposited Substrates of Gold by Atomic Force Microscopy: Influence of Substrate Topography on Anchoring of Liquid Crystals," *Chem. Mater.*, vol. 11, No. 3, pp. 612-623, 1999, published by American Chemical Society (Washington D.C.).

Shah, R.R. et al., "Using Liquid Crystals to Image Reactants and Products of Acid-Base Reactions on Surfaces with Micrometer Resolution," *J. Am. Chem. Soc.*, vol. 121, pp. 11300-11310, 1999, published by American Chemical Society (Washington D.C.).

Kim, S-R. et al., "Orientations of Liquid Crystals on Mechanically Rubbed Films of Bovine Serum Albumin: A Possible Substrate for Biomolecular Assays Based on Liquid Crystals," *Anal. Chem.*, vol. 72, No. 19, pp. 4646-4653, Oct. 1, 2000, published by the American Chemical Society (Washington D.C.).

Power Point presentation regarding "Optical Detection and Amplification of Biomolecular Interactions Using Liquid Crystals", by Jeff Brake and Nicholas Abbott, dated Apr. 26, 2000. Presented at the University of Wisconsin-Madison, Madison, Wisconsin, on Apr. 26, 2000.

Niculescu, M. et al., "Redox Hydrogel-Based Amperometric Bienzyme Electrodes for Fish Freshness Monitoring," *Anal. Chem.*, vol. 72, pp. 1591-1597, 2000, published by American Chemical Society (Washington D.C.).

Shah, R. R. et al., "Coupling of the Orientations of Liquid Crystals to Electrical Double Layers Formed by the Dissociation of Surface-Immobilized Salts," *J. Phys. Chem. B*, vol. 105, pp. 4936-4950, 2001, published by American Chemical Society (Washington D.C.).

Abbott, N. L. et al., "Imaging of Adsorption and Self-Organization of Amphiphiles at Aqueous-Liquid Crystals Interfaces," American Chemical Society Book of Abstracts, 221$^{st}$ National Meeting, Apr. 1-5, 2001.

Tingey, et al., "Orientations of Liquid Crystals on Chemically Functionalized Surfaces that Possess Gradients in Nanometer-Scale Topography," *Advanced Materials*, Sep. 2002, vol. 14, No. 17, pp. 1224-1227.

Encarta Dictionary—Biomolecule, Oct. 16, 2002, http://encarta.msn.com/.

Dark, G., The On-line Medical Dictionary, Oct. 16, 2002, http://cancerweb.ncl.ac.uk/omd/index.html.

Alberti et al., "Analysis of Complement C3 Deposition and Degradation on Kiebsiella Pneumoniae," *Infection and Immunity*, vol. 64, No. 11, pp. 4726-4732, 1996.

Fergason, J., "Liquid Crystals," *J. Sci. Amer.*, vol. 211, pp. 77-83, 1964.

Kolesar, Jr., E. et al. "Organophosphorus Compound Detection with a Supported Copper + Cuprous Oxide Island Film. 1. Gas-Sensitive Film Physical Characteristics and Direct Current Studies," *Anal. Chem.*, vol. 60, No. 17, pp. 1731-1736, Sep. 1, 1988.

Kolesar, Jr., E. et al., "Organophosphorus Compound Detection with a Supported Copper + Cuprous Oxide Island Film. 2. Alternating Current Studies and Sensor Performance," *Anal. Chem.*, vol. 60, No. 17, pp. 1737-1743, Sep. 1, 1988.

Nuzzo, R. G. et al., "Fundamental Studies of Microscopic Wetting on Organic Surfaces. 1. Formation and Structural Characterization of a Self-Consistent Series of Polyfunctional Organic Monolayers," *J. Am. Chem. Soc.*, vol. 112, pp. 558-569, 1990.

Bechhoefer, J. et al., "Systematic Studies of the Anchoring Transition in Nematic Liquid Crystals," *Physical Review A*, vol. 41, No. 6, pp. 3187-3191, Mar. 15, 1990; published by The American Physical Society.

Pieranski, P. et al., "Adsorption-Induced Anchoring Transitions," *Mol. Cryst. Liq. Cryst.*, vol. 179, pp. 285-315, 1990; published by Gordon and Breach Science Publishers S.A., printed in the United States of America.

Bechhoefer, J. et al., "Anchoring Transitions of Nematic Liquid Crystals," *Phase Trans.*, vol. 33, pp. 227-236, 1991; published by Gordon and Breach Science Publishers S.A., printed in the United Kingdom.

Kepley, L. J. et al., "Selective Surface Acoustic Wave-Based Organophosphonate Chemical Sensor Employing a Self-Assembled Composite Monolayer: A New Paradigm for Sensor Design," *Anal. Chem.*, vol. 64, pp. 3191-3193, Dec. 15, 1992.

Butler, M. A. et al., "Fiber Optic Micromirror Studies of the Interaction of Thin Copper Films with an Organophosphonate," *Anal. Chem.*, vol. 64, No. 17, pp. 1851-1854, Sep. 1, 1992.

Milanko, O. S. et al., "Evaluation of coating materials used on piezoelectric sensors for the detection of organophosphorus compounds in the vapour phase,"*Anal. Chem. Acta*, vol. 269, pp. 289-300, 1992; published by Elsevier Science Publishers B.V.

Jerome, B. et al., "Anchoring of nematic liquid crystals on mica in the presence of volatile molecules," *Physical Review E*, vol. 48, No. 6, pp. 4556-4574, Dec. 1993; published by The American Physical Society.

Yao, S., et al., "Circuit network analysis method applied to surface acoustic wave impedance system in liquids," *Anal. Chim. Acta*, vol. 294, pp. 311-318, 1994; published by Elsevier Science Publishers B.V.

Yang, L. et al., "Chemical Sensing Using Sol-Gel Derived Planar Waveguides and Indicator Phases," *Anal. Chem.*, vol. 67, No. 8, pp. 1307-1314, Apr. 15, 1995; published by American Chemical Society.

Wells., M. et al., "Interactions between Organized, Surface-Confined Monolayers and Vapor-Phase Probe Molecules. 9. Structure/Reactivity Relationship between Three Surface-Confined Isomers of Mercaptobenzoic Acid and Vapor-Phase Decylamine," *Langmuir*, vol. 12, No. 8, pp. 1989-1996, 1996.

Crooks, R. M., "Interactions between self-assembled monolayers and an organophosphonate," *Faraday Discuss.*, vol. 107, pp. 285-305, 1997.

Jenkins, A. L. et al., "Polymer Based Lanthanide Luminescent Sensors for the Detection of Nerve Agents," *Anal. Comm.*, vol. 34, pp. 221-224, Aug. 1997.

Swager, T. M., "The Molecular Wire Approach to Sensory Signal Amplification," *Acc. Chem. Res.*, vol. 31, No. 5, pp. 201-207, 1998; published by American Chemical Society.

Bertilsson, L. et al., "On the Adsorption of Dimethyl Methylphosphonate on Self-Assembled Alkanethiolate Monolayers: Influence of Humidity," *Langmuir*, vol. 15, No. 4, pp. 1128-1135, 1999; published by American Chemical Society.

Jenkins, A. L. et al., "Polymer-Based Lanthanide Luminescent Sensor for Detection of the Hydrolysis Product of the Nerve Agent Soman in Water," *Anal. Chem.*, vol. 71, No. 2, pp. 373-378, Jan. 15, 1999; published by American Chemical Society.

\* cited by examiner 1 mm 1 mm 1 mm 0.4 mm 1 mm

FIG. 21

The Effect of liquid crystals on VSV infectivity¶.

| Liquid Crystals | 7% DSCG | 30% A₃ | 21% C₁₄AO | PBS control |
|---|---|---|---|---|
| 30 min | 2.0 x 10⁷* | 0 | 0 | 1.59 x 10⁷ |
| 1 hr | 1.5 x 10⁷ | 0 | 0 | 1.98 x 10⁷ |
| 4 hr | 1.45 x 10⁷ | 0 | 0 | 1.58 x 10⁷ |

¶ VSV ($2 \times 10^7$ pfu) was incubated with different liquid crystals for periods of time, and the titer of virus was tested to determine if there was a reduction of infectious virus particles.

*Titer is reported as plaque forming unit (pfu); each plaque indicates one infectious virus particle in the inoculum.

LIQUID CRYSTALS WITH REDUCED TOXICITY AND APPLICATIONS THEREOF

CROSS-REFERENCES TO RELATED APPLICATIONS

This application claims priority to U.S. patent application Ser. No. 10/892,827, filed on Jul. 16, 2004, which in turn claims the benefit of U.S. Provisional Application No. 60/488,065 filed Jul. 17, 2003, the entire disclosures of which are incorporated herein by reference in their entirety and for all purposes as if fully set forth herein.

GOVERNMENT RIGHTS

This invention was made with United States government support awarded by the following agency: NSF 0079983. The United States has certain rights in this invention.

FIELD OF THE INVENTION

The invention relates generally to liquid crystal compositions for use with cells, to cell growth or culture media that includes liquid crystals, to methods for preparing cell growth media that includes liquid crystals, to devices and methods for growing cells in the presence of liquid crystals, and to methods of analyzing cells using liquid crystals.

BACKGROUND OF THE INVENTION

Enumeration of cell number and determining the spatial distribution of cells has wide applicability to biological research. It is the basis of assays for the study of compounds that promote or inhibit cell proliferation, cell adhesion, and cell migration at cell invasion into extracellular matrices. All of these in vitro assays are used in studies of fundamental biology as well as in assessing the potential therapeutic benefits of investigational compounds. Direct optical counting of cells for cell enumeration is in many respects considered the gold standard. See Sheppard, B. C., Rutten. M. J., Meichsner, C. L., Bacon, K. D., Leonetti, P. O., Land, J., Crass, R. C., Trunkey, D. D., Deveney, K. E., Deveney, C. W., Cancer, 85, 1454-64 (1999); Dunk, C., Ahmed, A., Am. J. Pathol. 158, 265-273 (2001). These methods are labor intensive, however, which has motivated the development of a wide array of indirect methods (e.g., MTT, Calcein AM which act as intracellular enzyme cleavage substrates) for use in determining cell number in assays of cell proliferation and cell migration. With few exceptions, methods integrating enumeration of cell number with spatial location available for the study of cell migration are very laborious, can consume large amounts of cells and reagents, and are generally not amenable to development of the high throughput systems needed to accelerate drug discovery and development of lead compounds for clinical applications. This is especially true for assays capable of separating out an increase in random cell movement (chemokinesis) from directed cell movement in response to a stimulus gradient (chemotaxis). Liquid crystal reporting systems have recently been disclosed for various purposes and could potentially meet all or many of these largely unmet needs. The missing element, however, in making this a truly robust technology for broad application is liquid crystals that exhibit reduced, little, or no toxicity to cells and a liquid crystalline cell culture media that supports normal cell function. Therefore, there is a need for liquid crystal compositions that exhibit reduced, little, or no toxicity to cells to which they are exposed as well as for new cell culturing media that includes liquid crystals that have reduced, little, or no toxicity to the cells being cultured or investigated.

Recently, liquid crystals have begun to be employed as novel and useful tools for application in devices for use in the physical and life sciences. Gupta, V. K., Skaife, J. J., Dubrovsky, T. B., Abbott, N. L., Science, 279, 2077 (1998); Luk, Y.-Y., Tingey, M. L., Hall, D. J., Israel, B. A., Murphy, C. J., Bertics, P. J., and Abbott, N. L., Langmuir, 19, 1671 (2003); Kim, S. R., Abbott, N. L., Langmuir, 18, 5269 (2002); Kim, S. R., Abbott, N. L., Adv. Mater., 13, 1445 (2001); Shah, R. R., Abbott, N. L., Science, 293, 1296 (2001). For example, nematic crystals have been reportedly used to amplify protein binding events on receptor decorated self-assembled monolayers (SAMs) supported on gold films that possess nanometer-scale topography. By using buffed films of biotinylated bovine serum albumin (BSA) covalently immobilized on glass substrates, liquid crystals have been exploited to detect the binding of antibody to surface bound biotins. Finally, by using surfaces that present metal ions that bind mesogens, reversible detection of parts-per-billion (by volume) levels of chemical agents such as organophosphonates has been established. See U.S. Pat. Nos. 6,413,587 B1; 6,284,197 B1; and 6,288,292 B1 and Published U.S. Patent Application Nos. 2002/0004216 A1; 2002/0028451 A1; 2002/0055093 A1; 2002/0071943 A1; 2002/0142453 A1; 2002/0164604 A1; 2003/0071949 A1; and 2003/0099993 A1 for various applications employing or related to liquid crystals each of which is herein incorporated by reference in its entirety and for all purposes. U.S. Pat. No. 6,171,802 issued to Woolverton et al., and titled "Detection and Amplification of Ligands," is directed to systems for the detection of ligands, the systems comprising at least one receptor and am amplification mechanism coupled to the receptor. An amplified signal is produced as a results of receptor binding to the ligand. Examples of suitable amplification mechanisms include antibody-embedded liquid crystalline materials; use alpha-2-macroglobulin to encage an enzyme, whereby the enzyme is separated from its substrate by a receptor; and a receptor engineered to inhibit the active site of an enzyme online in the absence of a ligand.

Many biological tools require the use of eukaryotic and prokaryotic cells. Eukaryotic mammalian cells are probably the most widely used cells although many different types of cells have found increasingly important application. Examples include, but are not limited to, tools for basic research in cell physiology, high throughput drug screening, and development sensors using cells on a chip. Lodish, H., Berk, A., Zipursky, S. L., Matsudaira, P., Baltimore, D., Darnell, J., MOLECULAR CELL BIOLOGY 4th ed., (W. H. Freeman & Company) (1999); Kapur, R., Giuliano, K. A., Campana, M., Adams, T., Olson, K., Jung, D., Mrksich, M., Vasudevan, C., Taylor, D. L., Biomed. Microdevices, 1, 99 (1999); Straub, B., Meyer, E., Fromherz, P., Nat. Biotechnol., 19, 121 (2001). Given the ubiquitous presence of the liquid crystalline state in biological systems and the technological utility of liquid crystals, it is surprising that few examples of the use of liquid crystal technologies involving whole mammalian cells has been reported. Gooby, J. W., Liquid Crystals, 24, 25 (1998); Fang, J., Ma, W., Selinger, J. V., and Shashidhar, R., Langmuir, 19, 2865 (2003). Perhaps one factor that has thus far served to prevent or limit the use of liquid crystals in conjunction with living cells is that thus far there have not been any reports of liquid crystal systems that exhibit low toxicity to living cells.

Until now, reports with respect to the toxicity of liquid crystals to cells have been very limited. Takatsu, H., Ohnishi, H., Kobayashi, K. Becker, W., Seki, M., Tazume, M., Saito, H., Sirmon-Hettich, B., Naemura, S., Mol. Cryst. Liq. Cryst., 364, 171 (2001). Toxicity tests performed by industry have thus far focused on the hazards to human health rather than toxicity to isolated cells. However, the toxicity of liquid crystals with respect to living cells is what is most relevant to applications of liquid crystals in life science and biotechnology. Therefore, a need exists for liquid crystal compositions that exhibit low toxicity towards living cell. A need also exists for compositions that include liquid crystals that may be used to culture cells, and devices for use in culturing cells with media that includes liquid crystals which exhibit low toxicity to cells. A need also exists for compositions that include a virus or a cell and a liquid crystalline compound and for methods for investigating viruses that use liquid crystals. A need further exists for methods of investigating the binding between a ligand and a receptor with mixtures of non-amphiphilic liquid crystals and the ligand.

SUMMARY OF THE INVENTION

The present invention provides liquid crystals that exhibit low toxicity towards cells, compositions that include liquid crystals that exhibit low toxicity towards cells, cell culture media compositions that include such liquid crystals, and devices and kits for use in culturing cells in the presence of liquid crystals that exhibit low toxicity towards cells.

In one aspect, the invention provides a liquid crystal composition. The composition includes at least two different liquid crystal compounds. In the composition, the first liquid crystal and the second liquid crystal both include at least one fluorine group, and at least one of the first liquid crystal and the second liquid crystal comprises a fluorinated phenyl group. In one embodiment, the fluorinated phenyl group is a monofluorinated phenyl group and in some embodiments, the fluorinated phenyl group is a difluorinated phenyl group.

In one embodiment of the liquid crystal composition, at least one of the first liquid crystal or the second liquid crystal is a compound of the following formula wherein Z is a methyl, ethyl, propyl, butyl, pentyl, hexyl, heptyl, octyl, nonyl, decyl, undecyl, dodecyl, tridecyl, tetradecyl, pentadecyl, or hexadecyl group. In some embodiments, Z is a methyl, ethyl, propyl, butyl, pentyl, hexyl, heptyl, or octyl group. In some such embodiments, Z is a propyl, butyl, pentyl, hexyl, heptyl, or octyl group. In some such embodiments, both the first liquid crystal and the second liquid crystal are compounds of the following formula wherein Z is a propyl group in the first liquid crystal and Z is a pentyl group in the second liquid crystal

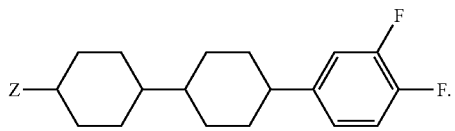

In some embodiments of the liquid crystal composition, the first liquid crystal is 4'-(3,4-difluorophenyl)-4-propylbicyclohexyl and the second liquid crystal is 4'-(3,4-difluorophenyl)-4-pentylbicyclohexyl and the molar ratio of the first liquid crystal to the second liquid crystal ranges from 10:90 to 90:10. In other such embodiments, the molar ratio of the first liquid crystal to the second liquid crystal ranges from 45:55 to 55:45, whereas in other such embodiments, the molar ratio of the first liquid crystal to the second liquid crystal is about 50:50.

In some embodiments of the liquid crystal composition, the liquid crystal composition further includes at least one cell culture medium component selected from a vitamin, an amino acid, a growth factor, or combinations of these. In some such embodiments, the liquid crystal composition further includes at least one vitamin and at least one amino acid.

In some embodiments of the liquid crystal composition, the liquid crystal composition further includes a cell and at least one cell culture medium component selected from a vitamin, an amino acid, a growth factor, or combinations of these. In some such embodiments, the cell is a stem cell, a 3T3 fibroblast, or a SV-40 transformed human corneal epithelial cell. In some embodiments, the cell is a mammalian cell. In some such embodiments, the cell is a human cell.

In another aspect, the invention provides a liquid crystal cell culture media that includes at least one liquid crystal and at least one cell culture component. The cell component is generally selected from a vitamin, an amino acid, a sugar, or combinations thereof, and the at least one liquid crystal compound includes at least one fluorine group, is a cholesteric liquid crystal, and/or is a liquid crystal that exhibits reduced toxicity towards cells.

In one embodiment of the liquid crystal cell culture medium, the cell culture media comprises at least three amino acids selected from the group consisting of L-alanine, L-arginine, L-asparagine, L-aspartic acid, L-cystine, L-glutamic acid, L-glutamine, glycine, L-histidine, hydroxy-L-proline, L-isoleucine, L-leucine, L-lysine, L-methionine, L-ornithine, L-phenylalanine, L-proline, L-serine, L-taurine, L-threonine, L-tryptophan, L-tyrosine, L-valine, salts and combinations thereof. In other such embodiments, the cell culture media includes at least four, at least five, at least six, at least seven, at least eight, at least nine, at least ten, or more of these amino acids or combinations thereof.

In some embodiments of the liquid crystal cell culture media, the cell culture media further comprises at least two salts selected from the group consisting of $CaCl_2$, NaCl, $NaHCO_3$, $Na_2HPO_4$, $NaH_2PO_4$, KCl, $K_2HPO_4$, $KH_2PO_4$, $MgSO_4$, $MgCl_2$, $Fe(NO_3)_3$, $FeSO_4$, $CuSO_4$, $ZnSO_4$, $ZnCl_2$, $CoCl_2$, $CuCl_2$, $MnCl_2$, $(NH_4)_2MoO_4$, and hydrates and combinations thereof. Some such embodiments include, at least three, at least four, at least five, at least six, or more such salts.

In other embodiments of the liquid crystal cell culture media, the cell culture media includes at least two vitamins selected from the group consisting of ascorbic acid, D-biotin, choline, choline chloride, choline bitartrate, folic acid, myo-inositol, inositol, niacin, niacinamide, nicotinamide, p-aminobenzoic acid, D-pantothenic acid, pyridoxine, pyridoxal, riboflavin, DL-thioctic acid, thiamine, vitamin B12, vitamin A alcohol, vitamin D-2, vitamin E, menadione, nicotinic acid, alpha-tocopherol, salts thereof, and combinations thereof. Some such embodiments include at least three, at least four, at least five, at least six, at least seven, at least eight, at least nine, at least ten, or more of these vitamins or combinations thereof.

In other embodiments of the liquid crystal cell culture media, the at least one liquid crystal is a cholesteric liquid crystal.

In other embodiments of the liquid crystal cell culture media, the at least one liquid crystal comprises a fluorinated cyclohexyl group.

In other embodiments of the liquid crystal cell culture media, the at least one liquid crystal comprises a fluorinated phenyl group. In some such embodiments, the fluorinated phenyl group is a monofluorinated phenyl groups, whereas in other embodiments, the phenyl group is a difluorinated phenyl group, is a trifluorinated phenyl group, is a tetrafluorinated phenyl group, or is a pentafluorinated phenyl group. In some embodiments, the fluorinated phenyl group is a 3,4- difluorophenyl group. In one such embodiment, the at least one liquid crystal comprises a difluorinated compound having the following formula where Z is an alkyl group having 1, 2, 3, 4, 5, 6, 7, 8, 9, 10, 11, 12, 13, 14, 15, or 16 carbon atoms. In one such embodiment, the at least one liquid crystal comprises a difluorinated compound having the following formula where Z is an alkyl group having 1, 2, 3, 4, 5, 6, 7, or 8 carbon atoms. In one such embodiment, the at least one liquid crystal comprises a difluorinated compound having the following formula where Z is an alkyl group having 3, 4, 5, 6, 7, or 8 carbon atoms

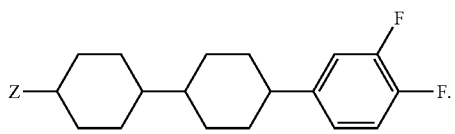

In other embodiments of the liquid crystal cell culture media, the at least one liquid crystal is a lyotropic liquid crystal.

In other embodiments of the liquid crystal cell culture media, the at least one liquid crystal is a thermotropic liquid crystal.

In other embodiments of the liquid crystal cell culture media, the liquid crystal cell culture media comprises 2, 3, 4, 5, or more different liquid crystals.

In other embodiments of the liquid crystal cell culture media, the liquid crystal cell culture media further comprises water.

In other embodiments of the liquid crystal cell culture media, the cell culture media further comprises a sugar such as glucose which may be dextrose.

In another aspect, the invention provides a kit for growing cells. Such kits include at least one liquid crystal selected from a cholesteric liquid crystal, a liquid crystal that includes at least one fluorine atom, and/or is a liquid crystal that exhibits reduced toxicity towards cells. Such kits also include a cell culture medium that includes at least one cell culture component selected from a vitamin, an amino acid, a sugar, or combinations thereof.

Various embodiments of the kit are provided in which the liquid crystal, the cell culture medium, or other components have any of the characteristics of the invention.

In some embodiments of the kit, the kit further includes at least one support for cells. In some such embodiments, the at least one support is transparent. In some such embodiments, the at least one support is a grid. In some embodiments, the at least one support is a permeable. In some embodiments, the at least one support includes a surface with topographic features that align liquid crystals on which cells may be placed. In some embodiments, the at least one support includes a surface with peaks on which cells may be placed.

In other embodiments, a kit includes instructions for growing cells in the cell culture medium in the presence of the at least one liquid crystal.

In another aspect the invention provides a device for growing cells in the presence of a liquid crystal. Such devices include liquid crystals of little or reduced toxicity as described herein, a container, and a support on which cells may be placed. Some such embodiments include a cell culture medium of the invention.

In other aspects, the invention provides methods for growing or culturing cells in the presence of a liquid crystal of reduced or no toxicity in accordance with the invention. The method includes growing cells in the presence of a liquid crystal of the invention using a cell culturing media of the invention.

In another aspect, the invention provides a composition that includes a virus and/or a cell, a compound of formula I or a salt thereof, and a cell culture component selected from a vitamin, an amino acid, a sugar, or combinations thereof. The compound of formula I has the following formula

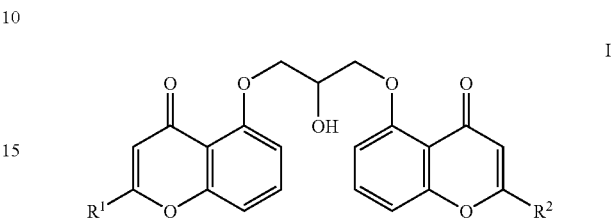

where, $R^1$ and $R^2$ are independently selected from —COOH, —N(tri $C_1$-$C_6$ alkyl)$^+$X$^-$, —CH$_2$SO$_3$H, —CH$_2$OSO$_3$H, or —O(CH$_2$CH$_2$O)$_n$CH$_2$CH$_2$OR; X$^-$ is an anion; n is an integer selected from 1, 2, 3, 4, or 5; and R is H or CH$_3$. In some such embodiments, the composition may include both the virus and the cell. In some embodiments X$^-$ is selected from Br$^-$, Cl$^-$, I$^-$, or F$^-$. In some embodiments, the virus is vesicular stomatitis virus. In some embodiments, the compound of formula I or the salt thereof is disodium chromoglycate. In still other embodiments, the composition further includes a poly-1-lysine coverslip.

In another aspect, the invention provides a method for investigating viruses. The method includes contacting a virus with a compound of formula I or a salt thereof, wherein the compound of formula I has the following formula

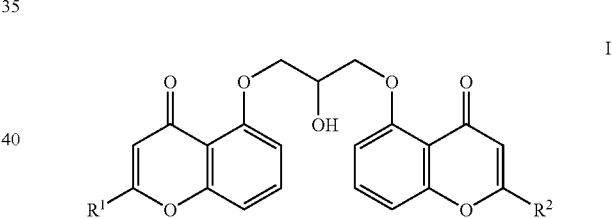

wherein, $R^1$ and $R^2$ are independently selected from —COOH, —N(tri $C_1$-$C_6$ alkyl)$^+$X$^-$, —CH$_2$SO$_3$H, —CH$_2$OSO$_3$H, or —O(CH$_2$CH$_2$O)$_n$CH$_2$CH$_2$OR; X$^-$ is an anion; n is an integer selected from 1, 2, 3, 4, or 5; and R is H or CH$_3$. Some such methods further include contacting the virus with the compound of formula I or the salt thereof in the presence of a cell. Still other such methods include contacting the virus with the compound of formula I or the salt thereof in the presence of the cell and a cell culture component selected from a vitamin, an amino acid, a sugar, or combinations thereof.

In another aspect, the invention provides a method for detecting interactions between a biomolecule and a receptor. The method includes contacting an aqueous solution comprising water, a liquid crystal, and a biomolecule with a surface that uniformly orients the liquid crystal when the biomolecule does not bind to a receptor. The receptor is either bound to the surface or is included in the aqueous solution. The surface resists adsorption of the biomolecule if the biomolecule does not bind to the receptor, but the biomolecule will be bound to the surface if the receptor is bound to the surface and the receptor binds the biomolecule. If the biomolecule binds to the receptor in the absence of the liquid crystal, then the biomolecule will still bind to the receptor in the presence of the liquid crystal. In some embodiments, the receptor is a protein.

In some embodiments of the method, the biomolecule is selected from a peptide, a polypeptide, DNA, RNA, a DNA fragment, a RNA fragment, a cell, a virus, or a bacterium.

In some embodiments of the method, the liquid crystal is a compound of formula I with the properties described above. In some such embodiments, the liquid crystal is disodium chromoglycate.

In some embodiments of the method, the surface includes a serum albumin, and the serum albumin resists adsorption of biomolecules that do not bind to the receptor.

In some embodiments of the method, the receptor is included in the aqueous solution whereas in other embodiments the receptor is bound to the surface.

In some embodiments of the method, the surface includes a self-assembled monolayer on a metallized surface. In some such embodiments, the self-assembled monolayer is formed from a thiol having the formula HS—$(CH_2)_p$—$(OCH_2CH_2)_q$—OH, wherein p is an integer with a value of from 5 to 20 and q is an integer with a value of from 1 to 6. In some such embodiments, p is 11 and q is 3 or 4.

In some embodiments of the method, the surface comprises a glass surface that has been reacted with a compound of formula $(R^aO)_3Si$—$(CH_2)_s$—N=C=O and has then been reacted with the receptor, wherein $R^a$ is a straight or branched chain alkyl group having 1 to 6 carbon atoms and s is an integer having a value of from 2 to 6. In some such embodiments $R^a$ is a methyl, ethyl, or propyl group and s is 3.

Further objects, features and advantages of the invention will be apparent from the following detailed description when taken in conjunction with the accompanying drawings.

BRIEF DESCRIPTION OF THE DRAWINGS

FIG. 5A shows results for confluent cultures of SV-40 HCEC cells; FIG. 5B, for sub-confluent cultures.

FIG. 6A shows results for 3T3 fibroblasts; FIG. 6B, for SV-40 HCEC cells.

FIG. 11C (30% $A_3$ in $H_2O$); FIG. 11D (7% DSCG in DMEM medium); FIG. 11E (15% DSCG in $H_2O$); and FIG. 11F (21% $C_{14}AO$ in $H_2O$ (3% $C_{10}OH$))) for 30 minutes. FIG. 11A is a control with the cells in PBS.

FIG. 12C (30% $A_3$ in $H_2O$); FIG. 12D (7% DSCG in DMEM medium); FIG. 12E (15% DSCG in $H_2O$); and FIG. 12F (21% $C_{14}AO$ in $H_2O$ (3% $C_{10}OH$))) for 4 hours. FIG. 12A is a control with the cells in PBS.

FIG. 13C (30% $A_3$ in $H_2O$); FIG. 13D (7% DSCG in DMEM medium); FIG. 13E (15% DSCG in $H_2O$); and FIG. 13F (21% $C_{14}AO$ in $H_2O$ (3% $C_{10}OH$))) for 4 hours and allowed to grow in medium for 4 days. FIG. 13A is a control with the cells in PBS.

FIG. 21 is a schematic illustration showing virus growth results after contact with liquid crystals.

DETAILED DESCRIPT

Figure 1A:
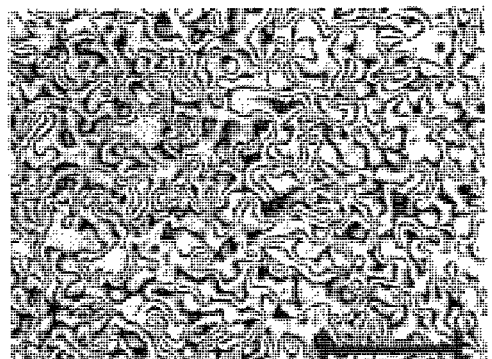
FIGS. 1A-1H are scanned images depicting optical images (crossed polars) of eight liquid crystals (see Tables 1 and 2 for a description of the composition and structure of the various liquid crystals) including the following: "E" Series (FIG. 1A); "A" Series (FIG. 1B); "B" Series (FIG. 1C); "C" Series (FIG. 1D); Cholesteric Series (FIG. 1E); E7 (FIG. 1F); 5CB (FIG. 1G); and TL205 (FIG. 1H).
Figure 1B:
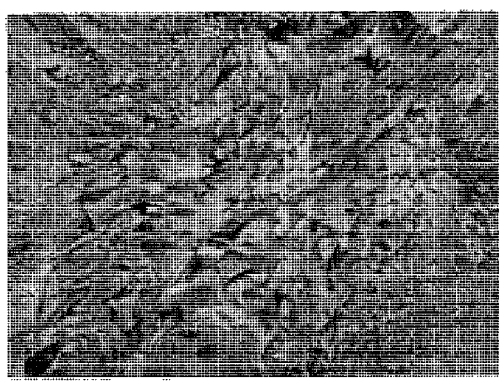
Figure 1C:
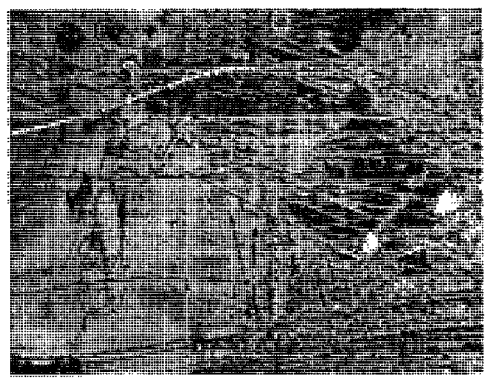
Figure 1D:
Figure 1E:
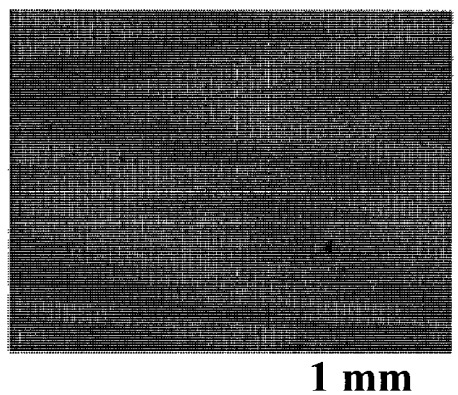
Figure 1F:
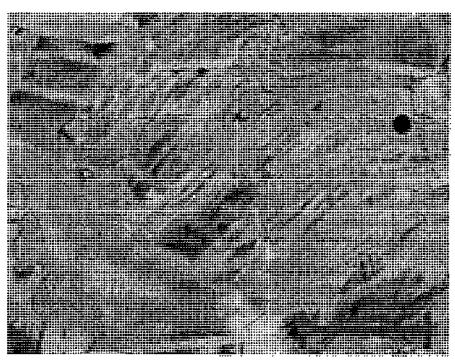
Figure 1G:
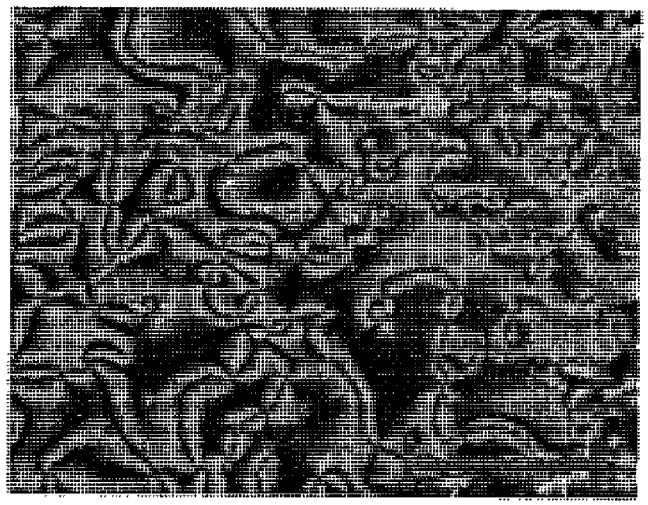
Figure 1H:

The term "BSA" refers to bovine serum albumin.

The term "DSCG" refers to disodium chromoglycate, a lyotropic liquid crystal compound having the formula

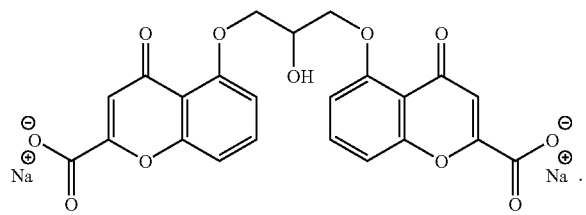

The term "$A_3$" refers to a tri-substituted 1,3,5-trimethyl-benzene compound having the following formula

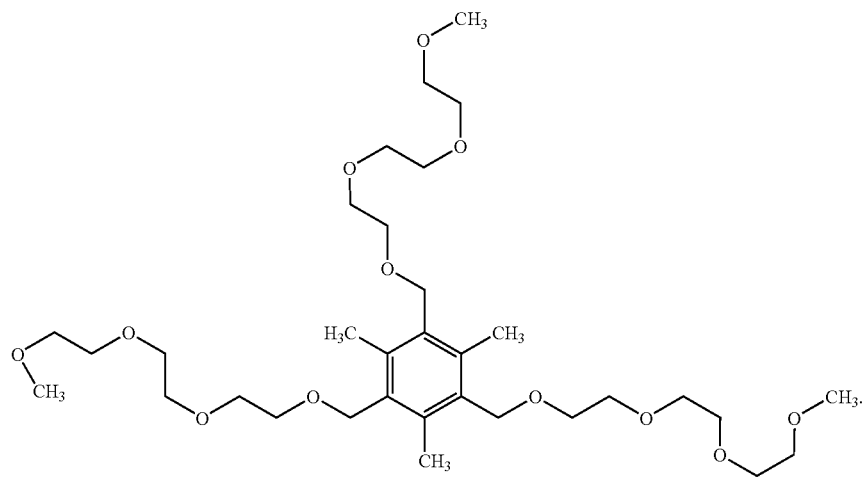

The term "$C_{14}AO$" refers to a mixture of an N-oxide compound and an alkanol compound having the following formulas

AMO

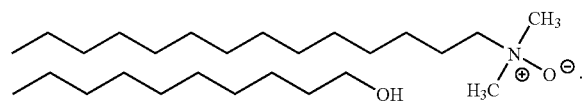

The term "EDTA" refers to ethylenediaminetetraacetic acid, a compound having the formula $(HO_2CCH_2)_2NCH_2CH_2N(CH_2CO_2H)_2$ and metal chelating properties.

All ranges recited herein include all combinations and subcombinations included within that range's limits. For example, a range of from about 0.2 μm to about 1 cm includes ranges of from 0.2 μm to 1 cm, of from 20 μm to 1 cm, of from 20 μm to 5,000 μm, of from 30 μm to 1 cm, of from 25 μm to 600 μm, of from 25 μm to 5,000 μm, of from 50 μm to 1 cm, of from 50 μm to 600 μm, of from 100 μm to 1 cm, of from 100 μm to 600 μm, and measurements of and about 20 μm, of and about 50 μm, of and about 100 μm, of and about 500 μm, of and about 5,000 μm, and of and about 1 cm etc. Furthermore, one skilled in the art will recognize that any listed range can be easily recognized as sufficiently describing and enabling the same range being broken down into at least equal halves, thirds, quarters, fifths, tenths, etc. As non-limiting examples, each range discussed herein can be readily broken down into a lower third, middle third, and upper third, and can be broken down into a lower half and an upper half.

Generally, the invention provides liquid crystals that exhibit low or no toxicity towards cells, compositions that include such liquid crystals, cell culture media compositions that include such liquid crystals, and devices and kits for use in culturing cells in the presence of liquid crystals that exhibit low or no toxicity towards cells.

As described above, few examples of the use of liquid crystal technologies involving whole mammalian cells have been reported. Gooby, J. W., *Liquid Crystals*, 24, 25 (1998); Fang, J., Ma, W., Selinger, J. V., and Shashidhar, R., *Langmuir*, 19, 2865 (2003). One factor that has thus far served to prevent or limit the use of liquid crystals in conjunction with living cells is that thus far there have not been any reports of liquid crystal systems that exhibit low toxicity to living cells. Experiments were thus conducted using liquid crystals and liquid crystal compositions were discovered that exhibit little or no toxicity to living cells. Experiments using living cells immersed under eight thermotropic liquid crystal mixtures were conducted to screen for and ascertain chemical functionalities which do not adversely impact the viability of cells. Each liquid crystal mixture investigated was comprised of mesogens that contained a different and unique set of functional groups.

As noted above, a panel of eight thermotropic liquid crystals was investigated. This panel included a broad range of liquid crystals with respect to physical properties and chemical functional groups. Two permanent mammalian cell lines, 3T3 fibroblasts and SV-40 transformed human corneal epithelial cells (HCECs), were employed to ascertain the toxic effects of the eight liquid crystals towards these cells. The two cell lines were selected because the 3T3 fibroblast is an undifferentiated cell type that is widely used in research and the HCEC line represents a cell line that is known to be highly sensitive to its chemical and physical environment.

Because the materials used in the experiments are solids at ambient temperature in their pure form, mesogens with common sets of functional groups were mixed to create liquid crystalline phases at ambient temperature. Therefore, in some embodiments, a liquid crystal composition includes a mixture of liquid crystals that together provide a mixture with liquid crystalline phases as ambient temperatures. In other embodiments, a liquid crystal composition includes a mixture of liquid crystal compounds such that the composition exhibits a liquid crystalline phase at temperatures of from about 10° C. to about 50° C., of from about 20° C. to about 45° C., of from about 22° C. to about 40° C., of from about 25° C. to about 40° C., or of from about 35° C. to about 40° C. In some embodiments, the liquid crystal composition includes a mixture of liquid crystal compounds such that the composition exhibits a liquid crystalline phase at temperature of 37° C. or about 37° C. By using liquid crystalline phases comprised of different, unique sets of functional groups, the toxic effects of the liquid crystalline phases could be correlated with the chemical functional groups on the liquid crystals.

The structure, composition, and physical properties of the investigated liquid crystal compositions are presented in Table 1 and Table 2. As depicted in Table 1, the "E" series comprises the two olefins, 1-(4-ethyl-cyclohexyl)-4-[2-(4-pentyl-cyclohexyl)-ethyl]-benzene (65 mole %) and 1-ethyl-4-(4-pentyl-cyclohexyl)-benzene (35 mole %). Because the phenyl and cyclohexyl groups are common to all the liquid crystals investigated except the cholesteric and lyotropic liquid crystals, the "E" series of liquid crystal was labeled and considered as having no functional groups.

As shown in Table 1, the "A" series comprises a mixture of 1-ethoxy-4-(4-propyl-cyclohexyl)-benzene (55 mole %) and 1-ethoxy-4-(4-pentyl-cyclohexyl)-benzene (45 mole %), both of which contain the ether functional group. The "B" series comprises 4-ethyl-cyclohexanecarboxylic acid 4-ethoxy-phenyl ester (50 mole %) and 4-pentyl-cyclohexanecarboxylic acid 4-methoxy-phenyl ester (50 mole %), both of which contain the ether and ester functional groups. 4-cyano-4'-pentylbiphenyl (5CB) was included in the analysis because it is a widely studied liquid crystal that is useful in a wide variety of applications.

The mixture E7, a mixture of four different cyanobiphenyls compounds with different aliphatic chain lengths, was also investigated for toxicity effects. The composition of E7 has previously been analyzed by chromatography and disclosed by Cognard. It was concluded that E7 and 5CB share the same cyano (nitrite) functional group. Cognard, J., *Mol. Cryst. Liq. Cryst. Suppl. Ser.*, 1, 1 (1982).

The "C" series comprises two fluoro-substituted olefins of 4'-(3,4-difluorophenyl)-4-propylbicyclohexyl (50 mole %) and 4'-(3,4-difluorophenyl)-4-pentylbicyclohexyl (50 mole %). Both components of the mixture thus include fluorophenyl, and more specifically, difluorophenyl, groups. As described in Table 1, TL205 is a mixture of liquid crystals that also includes fluorinated groups, in this case cyclohexane-fluorinated biphenyls and fluorinated terphenyls with aliphatic chains containing 2-5 carbons, although the exact composition is proprietary (EMerck Co). TL205 is similar to the "C" Series with respect to the chemical functionality present in the mesogens. Finally, the cholesteric series that was investigated included four cholesteric molecules including cholesteryl chloride, cholesteryl oleyl carbonate, cholesteryl 2,4-dichlorobezoate, and cholesteryl nonanoate.

TABLE 1

Structure and Composition of Various Liquid Crystals.

| Liquid Crystal | Structure and Composition (mole ratio) |
|---|---|
| "E" Series | [structure] 65% |
| | [structure] 35% |
| "A" Series | [structure] 55% |
| | [structure] 45% |
| "B" Series | [structure] 50% |
| | [structure] |

TABLE 1-continued

Structure and Composition of Various Liquid Crystals.

| Liquid Crystal | Structure and Composition (mole ratio) |
|---|---|

5CB: 50% pentyl-biphenyl-CN structure, 100%

E7: Mixture of:
- pentyl-biphenyl-CN, 51%
- heptyl-biphenyl-CN, 25%
- heptyloxy-biphenyl-CN, 16%
- pentyl-terphenyl-CN, 8%

"C" Series: 
- propyl-bicyclohexyl-(3,4-difluorophenyl), 50%
- pentyl-bicyclohexyl-(3,4-difluorophenyl), 50%

TL205: Mixture of cyclohexane-fluorinated biphenyls and fluorinated terphenyls. (See text for details)

Cholesteric:
- 22.1%: Ch—Cl
- 24.3%: Ch—O—C(=O)—O—(CH$_2$)$_5$—CH$_3$
- 19.6%: Ch—O—C(=O)—(2,4-dichlorophenyl)
- 34%: Ch—O—C(=O)—O—(CH$_2$)$_6$—CH=CH—(CH$_2$)$_5$—CH$_3$

TABLE 1-continued

Structure and Composition of Various Liquid Crystals.

| Liquid Crystal | Structure and Composition (mole ratio) |
|---|---|
| Ch = | 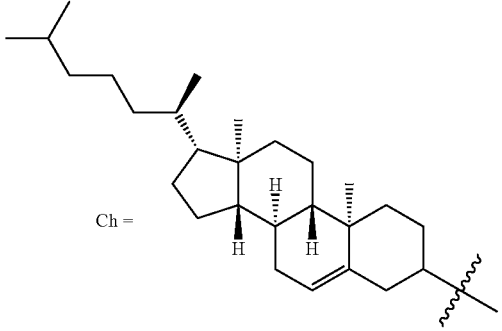 |

TABLE 2

Physical Properties of Liquid Crystals Used in Mammalian Cell Toxicity Tests

| Liquid Crystal | Mesophase[a] | Functional Groups | Transition temperature[b] | $\epsilon_{\parallel}, \epsilon_{\perp}$[c] | $n_e, n_o$[d] | $\rho$ (g cm$^{-3}$)[e] |
|---|---|---|---|---|---|---|
| "E" Series | Nematic | None | C < 19m53 I | — | — | — |
| "A" Series | Smectic | —O— | C < 19m38 I | — | — | — |
| "B" Series | Smectic | —O—, —COO— | C < 19m55 I | — | — | — |
| 5CB | Nematic | —CN | C22.5m35 I | 19.7, 6.7 | 1.7360, 1.5442 | 1.0065 |
| E7 | Nematic | —CN | M58I | 19.0, 5.2 | 1.7464, 1.5211 | — |
| "C" Series | Nematic | Fluorophenyl | C < 19m108I | — | — | >1 |
| TL205 | Nematic | Fluorophenyl | M87.4I | 9.1, 4.1 | 1.7445, 1.5270 | >1 |
| Cholesteric Series | Cholesteric | —Cl, —O(C=O)O— | N*73-75I | — | — | — |

[a] The mesophases reported here correspond to 22° C.
[b] The transition temperature between C(Crystalline), m(mesophase), N* (chiral nematic) and isotropic (I) phases.
[c] $\epsilon_{\parallel}$ and $\epsilon_{\perp}$ are the dielectric permittivities parallel and perpendicular to the direction of the liquid crystal, respectively.
[d] $n_e$ and $n_o$ are the two principal refractive indices corresponding to extraordinary ($n_e$) and ordinary ray ($n_o$) of refracted light.
[e] $\rho$ is the density of the liquid crystal.

A number of thermotropic liquid crystals that were not toxic to mammalian or other cells has been discovered. As described above, mesogenic molecules were mixed to create eight liquid crystal compositions each having a liquid crystalline phase each and a unique set of functional groups. The toxicity of each liquid crystalline phase was investigated using the two mammalian cell lines: 3T3 fibroblast and SV-40 transformed human corneal epithelial (HCEC) cells. Fluorescence assays were performed utilizing Calcein AM marker to assess the viability of the cells. Several classes of liquid crystals were identified that are not toxic to mammalian cells. Such liquid crystals included cholesteric liquid crystals and liquid crystals that contained fluorine atoms in groups such as fluorophenyl and fluorinated cyclohexyl groups. Notably, some of these reduced toxicity liquid crystals apparently stimulated the growth of cells during the period the cells were in contact with the liquid crystal.

Liquid Crystals

Various types of liquid crystals of reduced toxicity may be used in conjunction with any of the commercially available cell culture media to grow cells. Examples of suitable liquid crystals include, but are not limited to thermotropic and lyotropic liquid crystal. A large listing of liquid crystals is presented in "Handbook of Liquid Crystal Research" by Peter J. Collings and Jay S. Patel, Oxford University Press, 1997, ISBN 0-19-508442-X. Many of these may exhibit reduced toxicity or may be fluorinated to produce liquid crystals of reduced or no toxicity to cells. Although a variety of liquid crystals with reduced toxicity may be used in accordance with the invention, in some embodiments liquid crystals include one, two, three, four, or more fluorine atoms. In some such embodiments, the liquid crystal includes a fluorinated cyclohexane group, a fluorinated phenyl group, such as a monofluorinated phenyl group or a difluorinated group. In other embodiments, the liquid crystal is a fluorinated biphenyl or terphenyl compound, and in other embodiments, the liquid crystal of reduced cell toxicity is a cholesteric liquid crystal or a mixture of such compounds. In some embodiments, liquid crystal compositions of the invention include two, three, four, or more different liquid crystal species. An example of such a composition of reduced cell toxicity includes at least two types of liquid crystal that exhibit reduced or no toxicity towards cells. In some such compositions, each of the at least two types of liquid crystal includes at least one fluorine atom.

In other such compositions, one or two of the liquid crystals includes a fluorinated phenyl group or a fluorinated cyclohexyl group. In other such compositions, at least two of the liquid crystals include a fluorinated phenyl group or a fluorinated cyclohexyl group. In some such compositions, the fluorinated phenyl group is a monofluorinated phenyl group whereas in other such compositions, the fluorinated phenyl group is a difluorinated phenyl groups such as a 3,4-difluorophenyl group such as those shown in Table 1 for the "C" series. In one such composition, the liquid crystal composition includes at least two different liquid crystal species and one of the species is a 4'-(3,4-difluorophenyl)-4-propylbicyclohexyl and another of the species is 4'-(3,4-difluorophenyl)-4-pentylbicyclohexyl. Some such liquid crystal compositions only include these two types of liquid crystal although they may include other materials. In some such compositions, the mole ratio of one component to the other ranges from 10:90 to 90:10, from 20:80 to 80:20, from 30:70 to 70:30, from 40:60 to 60:40, from 45:55 to 55:45, and in some compositions the ratio of one component to the other is at or about 50:50 mole percent. One skilled in the art will appreciate that non-toxic liquid crystals or those with reduced toxicity may be combined in order to achieve desirable physical properties for example to achieve desired transition temperatures or ranges (See Table 2).

As noted above, various fluorine-comprising liquid crystal compounds can be used in accordance with the present invention. In some nonlimiting embodiments, a liquid crystal suitable for use in the present invention includes one having the formula R-A-L$^1$-B-L$^2$-C. In such embodiments, A, B, and C are independently selected from substituted and unsubstituted phenyl groups and substituted and unsubstituted cycloalkyl groups such as cyclohexyl groups, and the like. The cyclohexyl and/or phenyl groups of A, B, and C may be substituted with F, Cl, Br, I, hydroxy groups, alkoxy groups, alkyl groups, and the like. In compounds of formula R-A-L$^1$-B-L$^2$-C, L$^1$ and L$^2$ are linking groups and are independently selected from O, S, C(=O), OC(=O), and (CH$_2$)$_p$ groups where p is selected from 0, 1, 2, 3, 4, 5, or 6. In some embodiments, both L$^1$ and L$^2$ are (CH$_2$)$_p$ groups where p is selected from 0, 1, 2, 3, 4, 5, or 6. In some embodiments, p is selected from 0, 1, or 2. In some such embodiments, both L$^1$ and L$^2$ may be absent (p=0 for both L$^1$ and L$^2$) such that the compound has the formula R-A-B—C. In compounds of formula R-A-L$^1$-B-L$^2$-C, R is typically a straight chain or branched alkyl group. In some such embodiments R is an alkyl group which has 1, 2, 3, 4, 5, 6, 7, 8, 9, 10, 11, 12, 13, 14, 15, 16, 17, or 18 carbon atoms. In some such embodiments, R is a straight chain alkyl group which is a methyl, ethyl, propyl, butyl, pentyl, hexyl, heptyl, octyl, nonyl, or decyl group. In some such embodiments, R is a propyl, butyl, pentyl, hexyl, heptyl, or octyl group. In other embodiments, R is a propyl, butyl, pentyl, or hexyl group. Examples of compounds that are included within the formula R-A-L$^1$-B-L$^2$-C include the following classes of compound where n is selected from 0, 1, 2, 3, 4, 5, 6, 7, 8, 9, 10, 11, 12, 13, 14, 15, or 16, y is selected from 1, 2, 3, or 4, and x is selected from 1, 2, 3, 4, or 5. Kirsch, P. Bremer, M. *Angew. Chem. Int. Ed.* 39, 4216-4235 (2000).

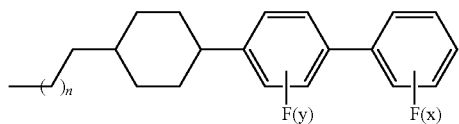

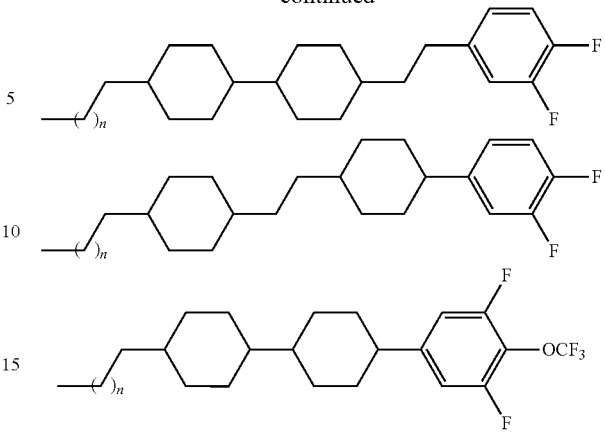

In some embodiments, the compounds of formula R-A-L$^1$-B-L$^2$-C include at least one fluorine atom. In other embodiments, the compounds of formula R-A-L$^1$-B-L$^2$-C include two, three, four, five, or more fluorine atoms. Some liquid crystal compositions suitable for use in the invention may include two or more different compounds of formula R-A-L$^1$-B-L$^2$-C where each of the different compounds comprises at least one fluorine atom. In some embodiments, the compounds of formula R-A-L$^1$-B-L$^2$-C include two cyclohexyl groups and one phenyl group. In other embodiments, the compounds include one cyclohexyl group and two phenyl groups.

Cell Culture Medium Components

Liquid crystals of reduced or no toxicity may be used in conjunction with any of the commercially available cell culture media to grow cells. In some embodiments, a liquid crystal comprising a fluorine atom is added to one or more components of a cell culture medium. In some embodiments, one more liquid crystals of reduced toxicity is/are added to a cell culture component selected from a salt, a vitamin, an amino acid, a sugar, or combinations thereof. In some such embodiments, the liquid crystal(s) is/are added to a commercially available cell culture medium. One skilled in the art will recognize that cell culture media may be selected based on the type of cell one is culturing and the application involved. Cells that may be cultured in conjunction with the current invention include both prokaryotic and eukaryotic cells. Examples of eukaryotic cells that may be cultured in the presence of the liquid crystals of reduced toxicity include mammalian, reptilian, avian, fish, amphibian, insect, and other cells. Mammalian cells such as human, monkey, ape, hamster, rat, guinea pig, mouse, dog, cat, horse, and cow cells may be cultured with the liquid crystal cell culture medium (LCCCM) of the invention. Plants cells may also be cultured using the LCCCM of the present invention. Virus, bacterial cells as well as chlamydial and mycoplasmal organisms may also be cultured using the LCCCM of the present invention. In some embodiments, the cells are selected from mouse, rat, hamster, guinea pig, monkey, ape, cat, dog, horse, pig, cow, plant, bacteria, or mycoplasmal cells. The LCCCM may also be used in conjunction with stem cells and stem cell research. Various cell culture medium components can be used alone or in conjunction with the liquid crystals and cell culture media of the present invention. Examples of suitable such cell culture media components, include, but are not limited to, inorganic salts, amino acids, vitamins, metals, sugars, growth factors, proteins, antibiotics, antifungal agents, antiviral agents, antimicrobial peptides, organic salts, dyes, HEPES, complex biological mixtures such as serum, brain-heart infusion, pituitary extracts, and the like. Many other cell culture media components suitable for use in the LCCCMs of the present invention may be found in Freshney's book which is herein incorporated by reference in its entirety. See Freshney, R. C. 2nd ed; Hardback; (Oxford University Press) (1992) ISBN: 019963212X. In one embodiment the LCCCM of the invention is used in conjunction with a cell, and the cell is grown in the LCCCM. In some such embodiments, a cell such as an embryonic stem cell is placed on the surface of a permeable interface and is grown in the LCCCM. A method of culturing cells in the presence of liquid crystals includes contacting a cell with a liquid crystal cell culture medium of the invention. In some such embodiments, the cell is contacted with the LCCCM for a period of 4 or more hours, of 6 or more hours, of 8 or more hours, of 12 or more hours, of 1 or more days, of 2 or more days, of 4 or more days, of 7 or more days, or of 2 or more weeks.

Various inorganic salts and their hydrates may be included as components in cell culture media that includes liquid crystals. Examples of such salts, include, but are not limited to, calcium salts such as, but not limited to, $CaCl_2$, and $CaCl_2.2H_2O$ and the like; sodium salts such as, but not limited to, NaCl, $NaHCO_3$, $Na_2HPO_4$, $NaH_2PO_4$, and the like; potassium salts, such as, but not limited to, KCl, $KH_2PO_4$, and the like; magnesium salts such as, but not limited to $MgSO_4$, $MgCl_2$, $MgCl_2.6H_2O$ and the like; and the like. Various other suitable inorganic salts include salts of transition metals including, but not limited to, salts of iron, cobalt, copper, zinc, manganese, molybdenum, and others. Examples of such salts include, but are not limited to, the following, their anhydrous forms, forms of different hydration, equivalents thereof, and the like: $Fe(NO_3)_3.9H_2O$, $FeSO_4.7H_2O$, $CuSO_4.5H_2O$, $ZnSO_4.7H_2O$, $ZnCl_2$, $CoCl_2.6H_2O$, $CuCl_2$, $MnCl_2.4H_2O$, $(NH_4)_2MoO_4.4H_2O$, and the like.

Various amino acids and their salts, where appropriate, may be included as components in cell culture media that includes liquid crystals. Examples of some such amino acids, include, but are not limited to, L-alanine, L-arginine, L-asparagine, L-aspartic acid, L-cystine, L-glutamic acid, L-glutamine, glycine, L-histidine, hydroxy-L-proline, L-isoleucine, L-leucine, L-lysine, L-methionine, L-ornithine, L-phenylalanine, L-proline, L-serine, L-taurine, L-threonine, L-tryptophan, L-tyrosine, L-valine, and the like.

Various vitamins and their salts may be included as components in cell culture media that includes liquid crystals. Examples of some such vitamins, include, but are not limited to, ascorbic acid, D-biotin, choline, choline chloride, choline bitartrate, folic acid, myo-inositol, inositol, niacin, niacinamide, nicotinamide, p-aminobenzoic acid, D-pantothenic acid, pyridoxine, pyridoxal, riboflavin, DL-thioctic acid, thiamine, vitamin B12, vitamin A alcohol, vitamin D-2, vitamin E, menadione, nicotinic acid, alpha-tocopherol, and the like.

Various sugars and carbohydrates may be as components included in cell culture media that includes liquid crystals. Examples of some such sugars, include, but are not limited to, glucose, dextrose, maltose, lactose, sucrose, and the like. One particular such sugar is D-glucose.

Various other ingredients and their salts may be included as components in cell culture media that includes liquid crystals. Examples of some such other ingredients, include, but are not limited to, phenol red, carbon dioxide, dihydrogen oxide, concanavalin A, pyruvic acid, sodium pyruvate, cytidine, dimethyl sulfoxide, hydrocortisone, hypoxanthine, thymidine, uridine, lectin, HEPES, succinic acid, linoleic acid, lipoic acid, putrescine, fumaric acid, alpha-ketoglutaric acid, L-malic acid, insulin, D-glucuronolactone, 5-methylcytosine, oxalacetic acid, NAD DPN, FAD, NADP TPN, uridine-5-triphosphate, 2-deoxycytidine, 2-deoxyadenosine, glutathione, cocarboxylase, Tween 80™ Coenzyme A, albumin, selenium, substance P, ethanolamine, ficoll, phosphoethanolamine, poly-l-lysine, poly-l-ornithine, dexamethasone, cholera toxin, adenine, fibronectin, collagen, lactic acid, laminin, heparin, retinol, thimerosal, thioctic acid, uracil, xanthine, vitronectin, and the like. Still other ingredients that may be included as components include bovine fetuin, transferrin, plant hydrolysates, Pluronic F68R, bovine serum albumin, methylcellulose, cytokines, and the like. Antimicrobials including, but not limited to, the following may also be included as components in the LCCCM of the present invention actinomycin D, ampicillin, chloramphenicol, kanamycin, nystatin gentamycin, penicillin, streptomycin, tetracycline, neomycin, fluconazole, amphotericin B, cecropin A, cecropin B, magainin 1, magainin 2, indolicidin, and the like. Growth factors, such as, but not limited to, the following may also be included in LCCCM of the invention: epidermal growth factor, fibroblast growth factor, hepatocyte growth factor, nerve growth factor, keratinocyte growth factor, platelet-derived growth factor, insulin-like growth factor 1, insulin-like growth factor 2, transforming growth factor-alpha, transforming growth factor-beta, endothelial cell growth factor, erythropoietin, interleukin 1a, interleukin 1b, interleukin 2, interleukin 3, interleukin 4, interleukin 5, interleukin 6, tumor necrosis factor, vascular endothelial growth factor, brain-derived neurotrophic factor, and the like. Complex biological additives may be included in the LCCCM of the invention, including, but not limited to, fetal bovine serum, newborn calf serum, horse serum, donkey serum, chicken serum, goat serum, porcine serum, rabbit serum, human serum, brain-heart infusion, bovine pituitary extract, and the like.

The liquid crystalline cell culture media of the invention are capable of supporting normal cell function after prolonged incubation. Cell culture media that include liquid crystals of low or no toxicity allow liquid crystal reporting technology to be used to investigate cellular phenomenon in real time. For example, assays of cell proliferation and cell migration may be repeatedly performed on the same population of cells to examine how it changes over time. The cell culture media of the invention may be used in conjunction with a wide variety of cells as discussed above. One application of the cell culture media of the present invention is in the culture of embryonic stem cells as will be apparent to one of skill in the art. Such culture media may be used, in conjunction with specifically fabricated nanostructured surfaces decorated with receptors for soluble markers of differentiation, to identify the state of differentiation of embryonic stem cells. This may be accomplished by combining the use of the liquid crystalline cell culture media with the nanostructured substrates in the references noted above and incorporated herein by reference. For example, in order to determine the state of differentiation of stem cells cultured in cell culture media of the invention could be used with a nanostructured substrate with specific receptors for differentiation markers immobilized on its surface. The unique properties of liquid crystals allow the cell culturing media of the invention to be used in other applications. For example, it is known that mechanical forces impinging on cells can modulate the differentiation process of cells grown in such media. Therefore, the liquid crystalline cell culture media may be used to influence and modulate the differentiation of stem cells. Notably, the use of liquid crystalline cell culture media of the invention does not prevent the use of more traditional reporting strategies such as fluorometric, enzymatic, or colorimetric reporting systems.

Figure 7:
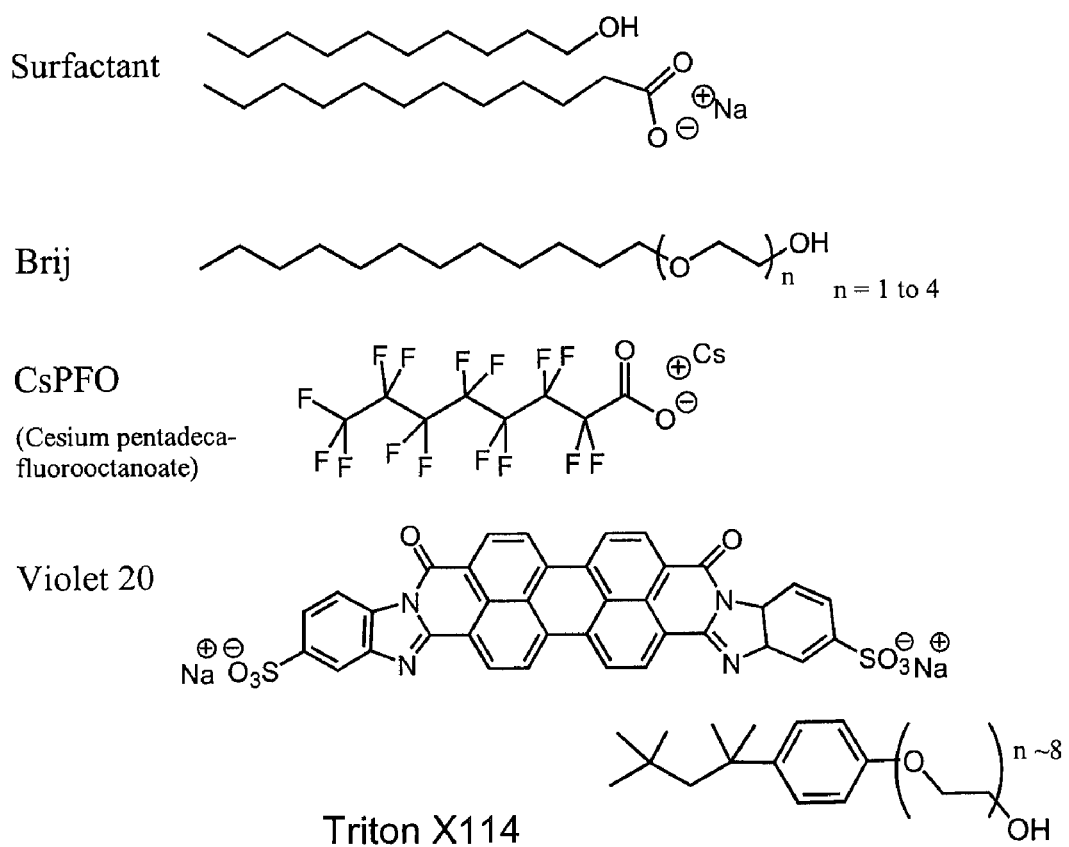
FIG. 7 depicts various compounds related to lyotropic liquid crystals and aqueous mixtures that are disclosed herein.
Figure 8:
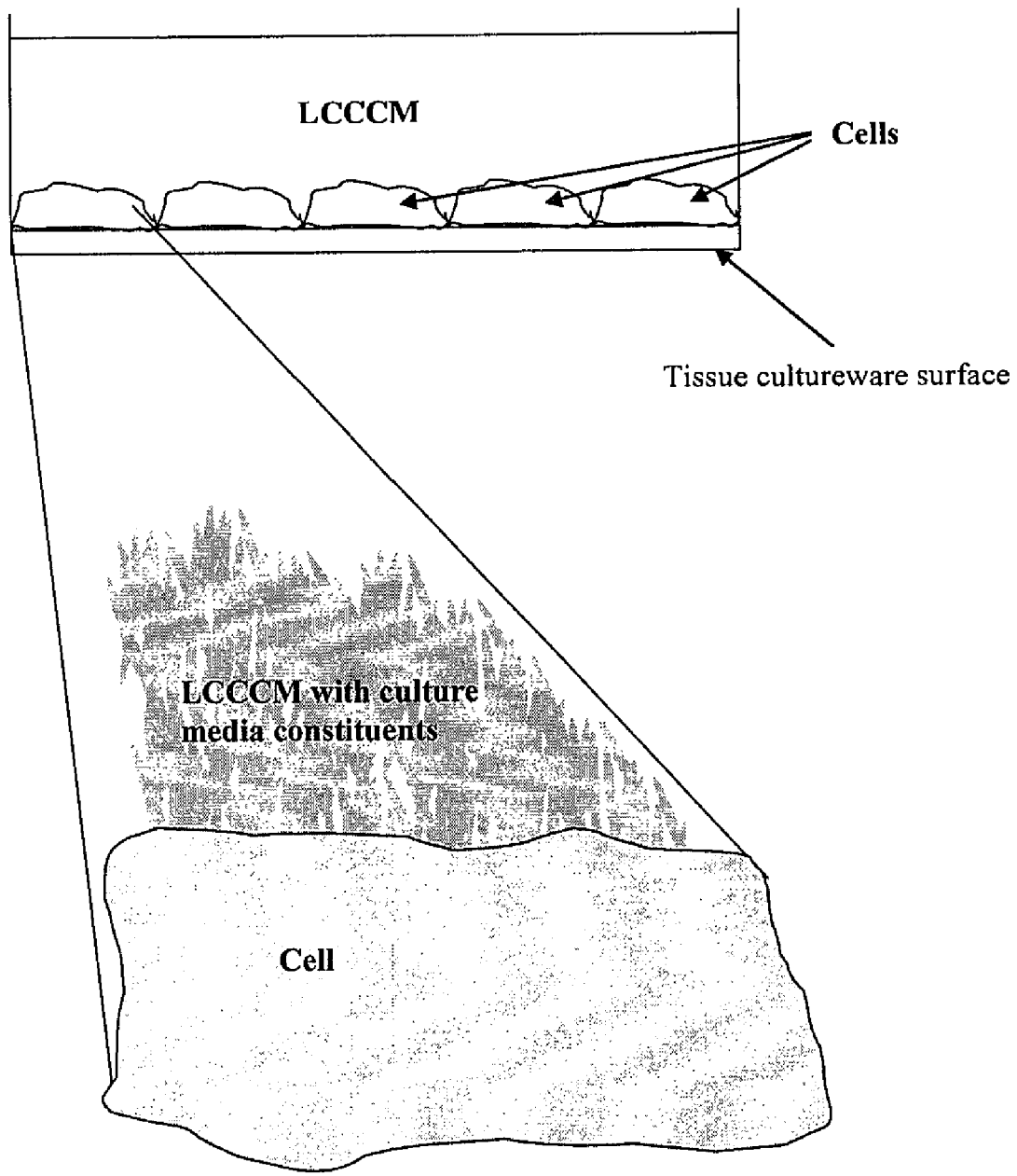
FIG. 8 depicts a device and method for growing cells in the presence of lyotropic liquid crystals.

As noted above, FIG. 8 depicts a device and method for growing cells in the presence of lyotropic liquid crystals. Because the phase of lyotropic liquid crystals is predominantly water, it is easy to dissolve nutrients, buffers, and trophic factors that are conventionally delivered to cells in the aqueous phase. Examples of compounds that form lyotropic liquid crystal phases are depicted in FIG. 7. Thus, water soluble cell culture constituents such as, but not limited to, amino acids; energy sources such as, but not limited to, glucose and the like; trophic factors such as, but not limited to, EGF and the like; antibiotics such as, but not limited to, gentamycin and the like can be solubilized in lyotropic liquid crystals. Other components such as those described above may also be employed with this system. This allows for the development of liquid crystalline cell culture media that can be used with standard cell culture procedures. As shown in FIG. 8, the liquid crystalline cell culture media (LCCCM) can be placed directly on the cells. Gas exchange has been indicated as adequate in early results and may be improved in the case of liquid crystals that include fluorine groups such as fluorophenyl groups. Provision of nutrients and removal of waste occurs through the LCCCM.

Due to the hydrophobic nature of thermotropic liquid crystals, the solubility of essential nutrients, buffers and trophic factors in the liquid crystal may be limiting. Therefore, cell culture in LCCCM that includes thermotropic liquid crystals is generally performed using different techniques. In one method, an amphiphilic species such as a phospholipid is incorporated in the liquid crystal. Microemulsions may be formed in nematic liquid crystals in which thermodynamically stable, nanometer-sized aqueous pools form spontaneously in the liquid crystal. These aqueous pools may act as nanoscopic carriers of aqueous nutrients, buffers, and trophic factors to the cells. A second approach that may be employed is the formation of nematic emulsions. In such embodiments, a thermotropic liquid crystal and an aqueous phase is emulsified in the presence of a stabilizer such as a phospholipid or a surfactant. The pools of aqueous phase dispersed in the liquid crystal provide nutrients, trophic factors, etc, during the contact of liquid crystal with the cells. In one method, a set up similar to that shown in FIG. 8 is used. In some methods, a non-toxic thermotropic liquid crystal species may be placed directly on the cells, and a surfactant is added to the non-toxic LCCCM such that reverse micelles of the liquid crystal are created. The micelles provide aqueous domains with the liquid crystal film that allows diffusion of nutrients from the aqueous phase to the cell.

Figure 9:
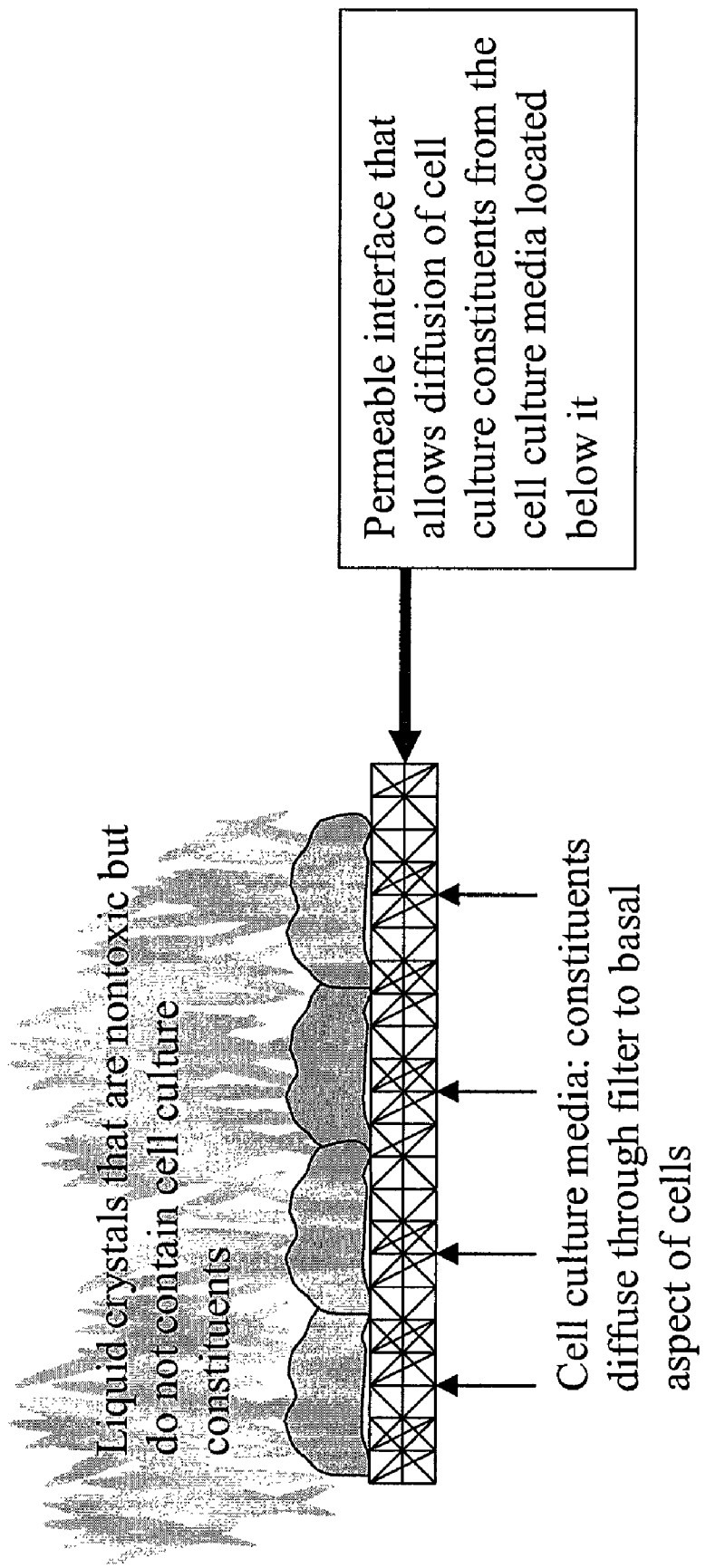
FIG. 9 depicts a device and method for growing cells in the presence of thermotropic and/or lyotropic liquid crystals in which cell culture media is located below a permeable interface on which cells are seeded.

As noted above, FIG. 9 depicts a device and method for growing cells in the presence of thermotropic and/or lyotropic liquid crystals. In the application shown in FIG. 9, cell culture media is located below a permeable interface or support that cells are seeded upon. In some embodiments, the permeable interface is transparent. Examples of a suitable permeable interface include, but are not limited to, perforated metallic supports such as TEM grids and the like, and polymeric filters such as, but not limited to, cellulose acetate and the like. Permeable interfaces may be formed using spin-casting techniques as will be known to those skilled in the art. The permeable interface generally allows normal cell attachment, should be non-cytotoxic, and allows diffusion of cell culture media components through it to the basal surface of cells seeded on the surface of the permeable interface. A liquid crystalline species (thermotropic or lyotropic) which exhibits low or no toxicity towards cells may be placed on the surface of the cells in such applications as shown in FIG. 9.

Figure 10:
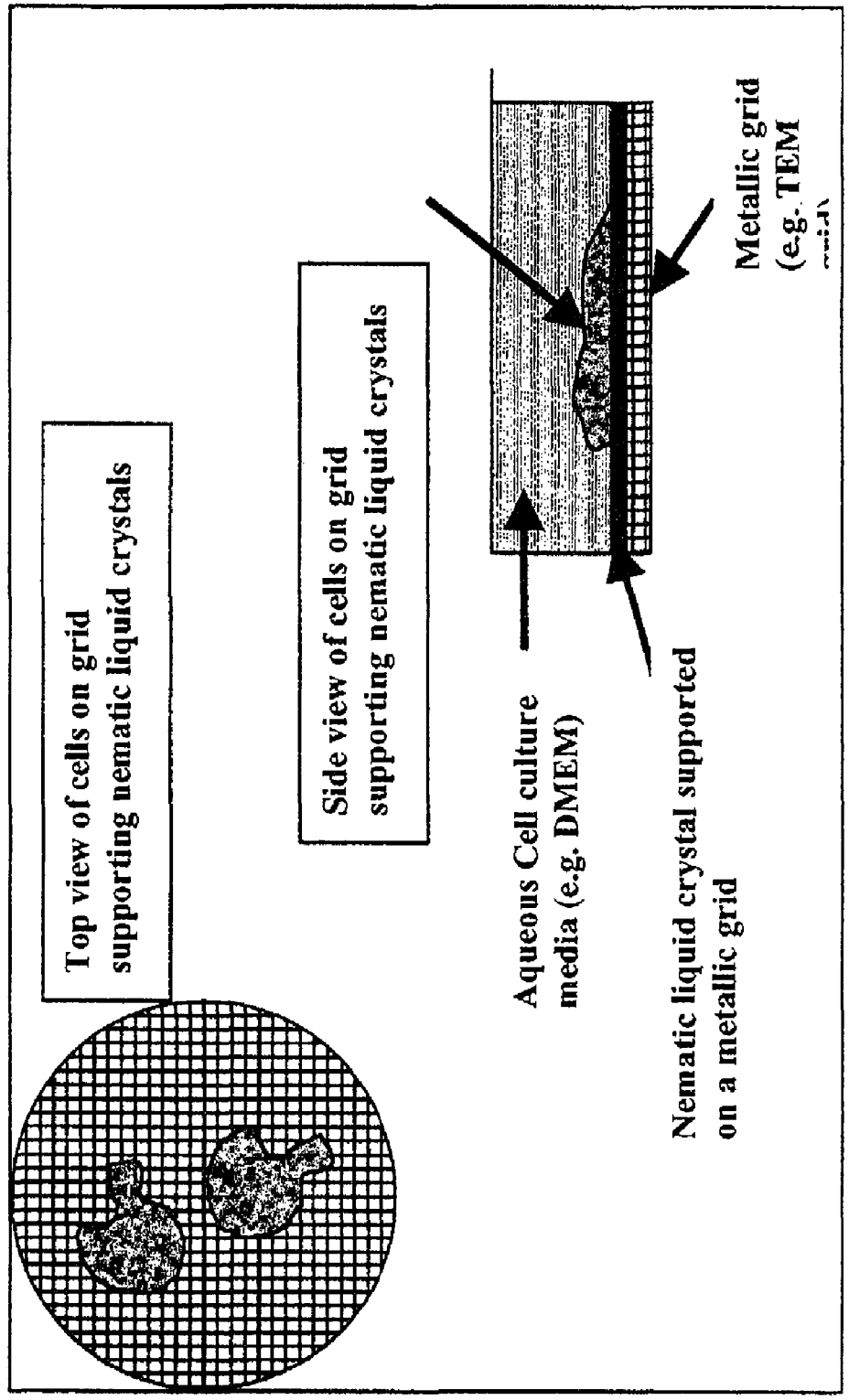
FIG. 10 depicts an embodiment of another device and method for growing cells in the presence of thermotropic and/or lyotropic liquid crystals using a cell support.
Figure 11A:
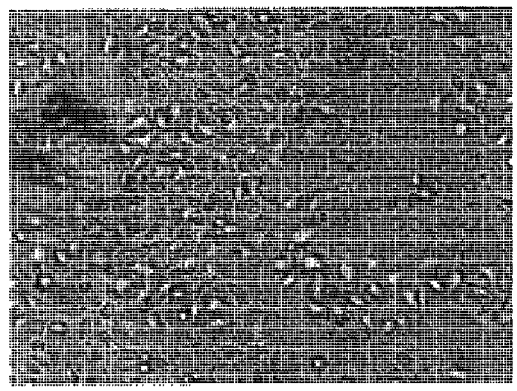
FIGS. 11A-11F are scanned images of HeLa cells (human cervical cancer cells) after contact with liquid crystals (FIG. 11B (7% DSCG in $H_2O$)
Figure 11B:
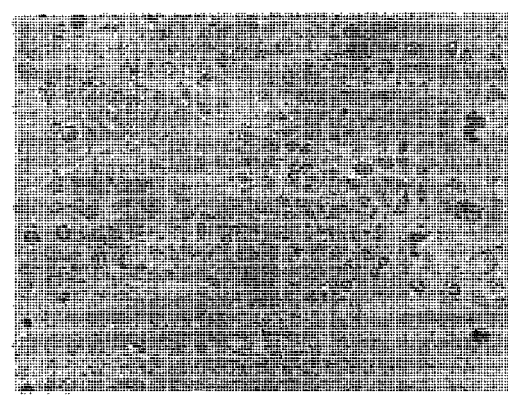
Figure 11C:
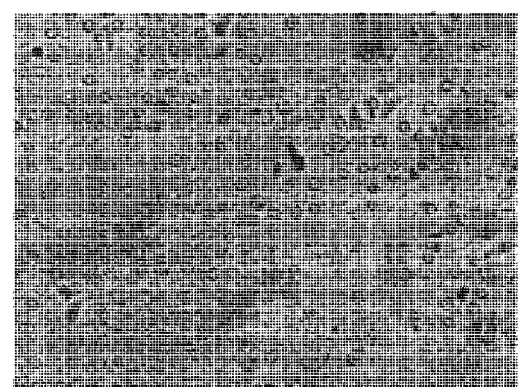
Figure 11D:
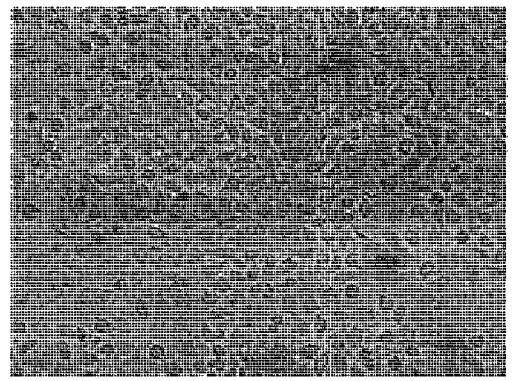
Figure 11E:
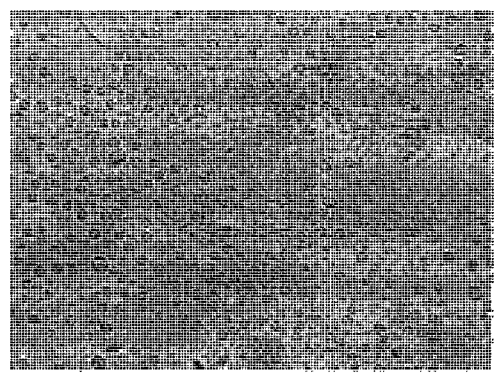
Figure 11F:
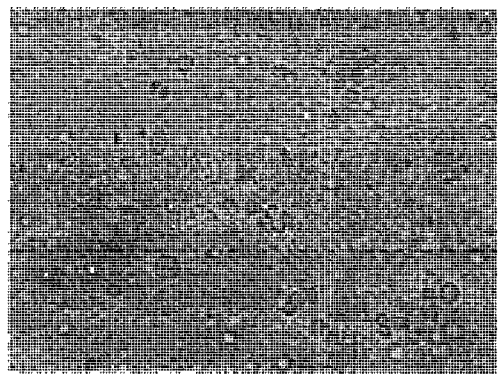
Figure 12A:
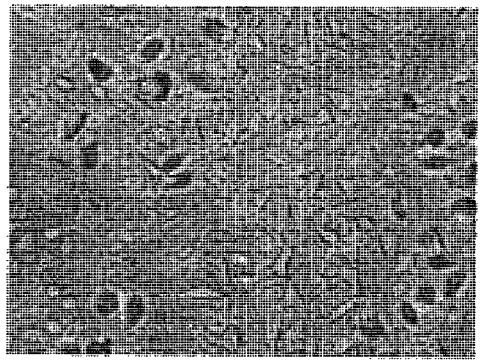
FIGS. 12A-12F are scanned images of HeLa cells (human cervical cancer cells) after contact with liquid crystals (FIG. 12B (7% DSCG in $H_2O$)
Figure 12B:
Figure 12C:
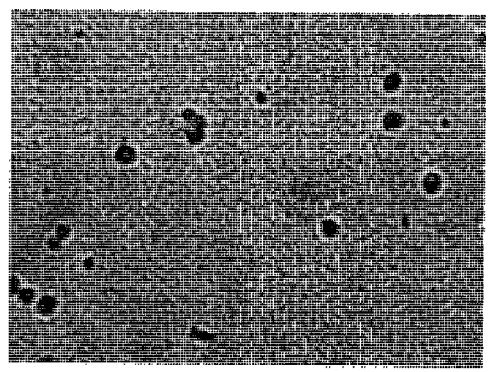
Figure 12D:
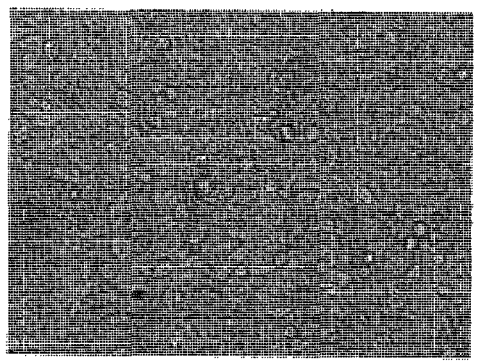
Figure 12E:
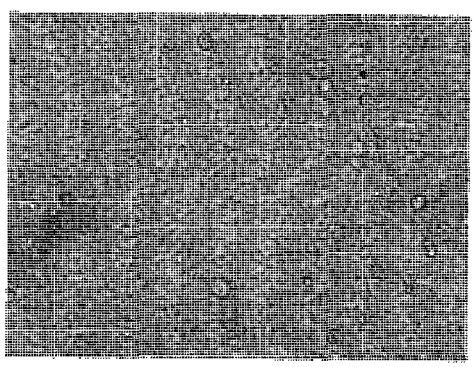
Figure 12F:
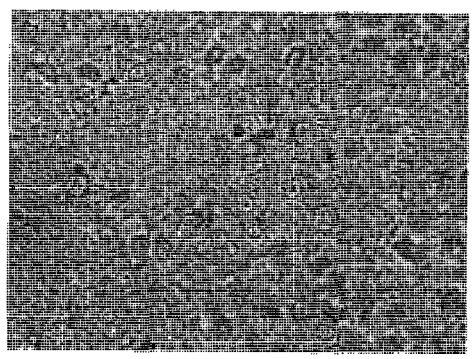
Figure 13A:
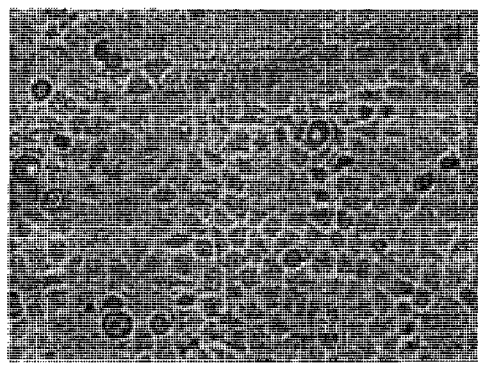
FIGS. 13A-13F are scanned images of HeLa cells (human cervical cancer cells) after contact with liquid crystals (FIG. 13B (7% DSCG in $H_2O$)
Figure 13B:
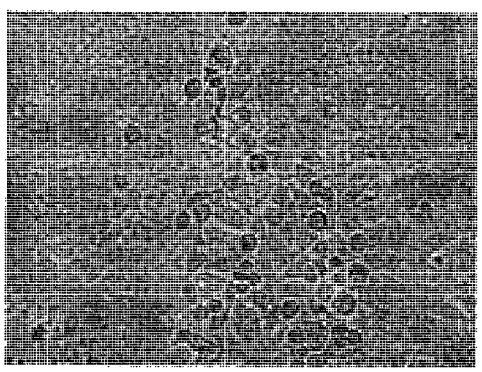
Figure 13C:
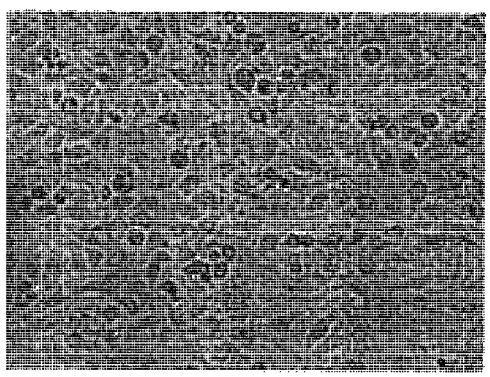
Figure 13D:
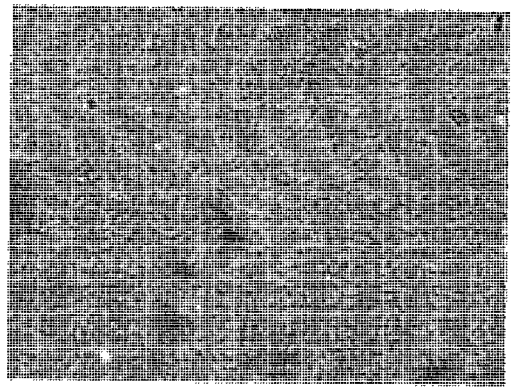
Figure 13E:
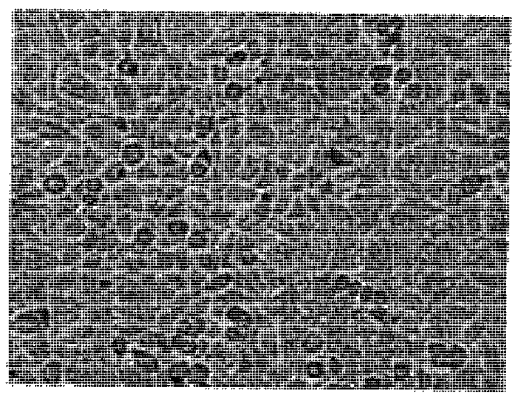
Figure 13F:
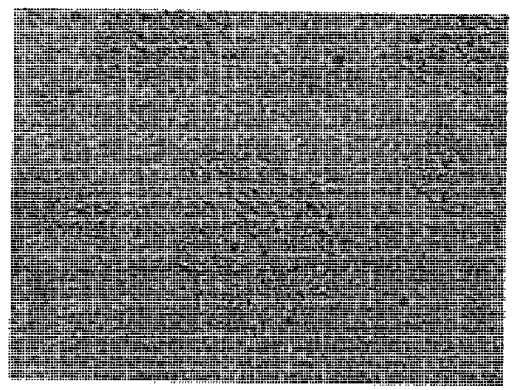

As indicated above, FIG. 10 depicts an embodiment of a device and method for growing cells in the presence of thermotropic and/or lyotropic liquid crystals using a cell support, such as, but not limited to a grid such as, but not limited to, a TEM grid or the like, and a nematic liquid crystal supported on the cell support. Nutrients in the cell culture media are able to reach the cells through the grid. In other alternative embodiments, the cell support has nanostructured to microstructures surface topographic features such as, but not limited to ridges, and grooves or columnar projections e.g. pillars, and the cell(s) is/are placed on the top of the ridges, peaks, pillars, columnar projections, or other similar feature or combinations thereof. In this manner, the cell culture media is able to reach the cells from the bottom even when they are covered with a liquid crystal that exhibits little or no toxicity towards the cells.

The invention further provides methods for detecting interactions between a biomolecule and a receptor. The method includes contacting an aqueous solution that includes water, a liquid crystal, and a biomolecule with a surface that uniformly orients the liquid crystal when the biomolecule does not bind to a receptor. The receptor is either bound to the surface or is included in the aqueous solution. The surface resists adsorption of the biomolecule if the biomolecule does not bind to the receptor, but the biomolecule will be bound to the surface if the receptor is bound to the surface and the receptor binds the biomolecule. If the biomolecule binds to the receptor in the absence of the liquid crystal, then the biomolecule will still bind to the receptor in the presence of the liquid crystal. In some embodiments, the receptor is a protein.

In some embodiments of the method for detecting interactions between a biomolecule and a receptor, the biomolecule is selected from a peptide, a polypeptide, DNA, RNA, a DNA fragment, a RNA fragment, a cell, a virus, or a bacterium.

In some embodiments of the method for detecting interactions between a biomolecule and a receptor, the liquid crystal is a compound of formula I with the properties described above. In some such embodiments, the liquid crystal is disodium chromoglycate.

In some embodiments of the method for detecting interactions between a biomolecule and a receptor, the surface includes a serum albumin, and the serum albumin resists adsorption of biomolecules that do not bind to the receptor.

In some embodiments of the method for detecting interactions between a biomolecule and a receptor, the receptor is included in the aqueous solution whereas in other embodiments the receptor is bound to the surface.

In some embodiments of the method for detecting interactions between a biomolecule and a receptor, the surface includes a self-assembled monolayer on a metallized surface. In some such embodiments, the self-assembled monolayer is formed from a thiol having the formula $HS—(CH_2)_p—(OCH_2CH_2)_q—OH$, wherein p is an integer with a value of from 5 to 20 and q is an integer with a value of from 1 to 6. In some such embodiments, p is 11 and q is 3 or 4.

In some embodiments of the method for detecting interactions between a biomolecule and a receptor, the surface comprises a glass surface that has been reacted with a compound of formula $(R^aO)_3Si—(CH_2)_n—N=C=O$ and has then been reacted with the receptor, wherein $R^a$ is a straight or branched chain alkyl group having 1 to 6 carbon atoms and s is an integer having a value of from 2 to 6. In some such embodiments $R^a$ is a methyl, ethyl, or propyl group and s is 3.

EXAMPLES

Various nematic liquid crystals were screened to investigate their toxicity with respect to animal cells. Calcein AM (Molecular Probes), an intracellular esterase cleavage substrate that increases fluorescence with cleavage, was used to report cell viability using 3T3 fibroblast and SV-40 transformed human corneal epithelial (HCEC) cells which were exposed to varying concentrations of the liquid crystal. After incubation, the liquid crystal was removed, the cells were rinsed, and Calcein AM was added in PBS. The amount of fluorescence, proportional to the number of viable cells, was determined using an automated fluorescence plate reader (Cytofluor 4000). Ethidium homodimer was also used to enumerate dead cells. Significantly, the liquid crystals that exhibited reduced toxicity to cells do so even after exposure of cells to pure liquid crystal for four hours.

The following materials and methodologies were utilized in the examples discussed in greater detail below.

Materials

Fetal bovine serum, dimethyl sulfoxide (DMSO), gentamycin, and ethylenediaminetetraacetic acid (EDTA) were purchased from Sigma Aldrich (St. Louis, Mo.). Phosphate buffered saline (PBS), Dulbecco's modified eagle medium (DMEM) and Ham's F-12 were purchased from BioWhittaker (Walkersville, Md.). 75 cm² culture flasks and 96-well plates were purchased from Fisher Scientific (Pittsburgh, Pa.). Calcein-AM and ethidium homodimer were purchased from Molecular Probes (Eugene, Oreg.). Porcine trypsin was purchased from JRH Biosciences (Lenexa, Kans.). The Cytofluor 4000 TC brand automated plate reader was purchased from PE Biosystems (Foster City, Calif.). 3T3 fibroblasts were purchased from ATCC (Rockville, Md.). SV-40 transformed human corneal epithelial cells were provided as a gift from Dr. Kaora Araki-Sasaki of Kinki Central Hospital.

Liquid Crystals. TL205, 5CB, and E7 were purchased from EM industries (Merck), (Hawthorne, N.Y.). Components for the cholesteric series were purchased from Pressure Chemical Company (Pittsburgh, Pa.). Components for the "A", "B", "C" and "E" series were purchased from Phentex Corporation, (Richardson, Tex.).

Formation of Optical Cells for Imaging of Liquid Crystals

The glass microscope slides employed in the experiments were Fisher's Finest, premium grade obtained from Fisher Scientific (Pittsburgh, Pa.). The optical cells used to record the textures of the liquid crystals were fabricated by one of two methods. 5CB, "E", "B" or "A" series liquid crystals were heated above their clearing temperatures, and then introduced between two sandwiched glass substrates that were spaced by a 12 μm thick Saran wrap. The isotropic phases filled the optical cells by capillary motion. For the "C" series, TL205, E7 or cholesteric liquid crystals, a drop of the liquid crystal was placed onto one of the two glass substrates with the Saran wrap spacer in place, and then was compressed by the other glass substrate to afford an optical cell.

X-ray Diffractometry

Polycrystalline diffraction patterns for the liquid crystals 5CB, 8CB, "E", "A", "B", "C" and "D" series were collected on a Siemens Analytical X-Rays Instrument. The liquid crystals were injected into capillary tubes (2 mm in diameter, (Hampton Research, CA)). Data were collected with Cu Kα radiation using an incident beam monochromator ($\lambda=1.54$ Å) on an area detector.

Cell Culture

3T3 fibroblasts were cultured in DMEM (supplemented with 10% fetal bovine serum plus 40 μg/ml gentamycin) and grown in a humidified incubator at 37° C. and 5% $CO_2$. SV-40 HCEC were cultured in supplemented hormonal epithelial medium (SHEM)—a basal medium for epithelial cell growth—with 10% fetal bovine serum. SHEM is a mixture of DMEM and Ham's F-12 (50/50) plus 0.5% DMSO and 40 μg/ml gentamycin. The hormones were not added in these experiments. The culture media was changed every other day for both cell types until the cells reached a confluency of 90-95% at which time they were passaged using trypsin/EDTA (~0.25%/25 M).

Viability/Cytotoxicity Assays

Cells were plated at a concentration of 10,000 cells/well on a 96-well plate and allowed to attach and proliferate overnight. Media was removed, and various liquid crystals and PBS were added (25 μL/well). PBS was used as a control. Cells were incubated at 37° C. for 4 hours, at which time the liquid crystals were removed by washing three times with PBS. 50 μL of Calcein-AM (0.6 μM) was added to each well, and the plate was incubated for an additional 2 hours to allow for an increase in fluorescence. Fluorescence was measured at 485 nm using 530 nm excitation from a Cytofluor 4000 TC automated plate reader.

Mesophases of Liquid Crystal Materials

The mesogens comprising the "E", "A", "B", and "C" series are solid or isotropic at room temperature. Compositions of mixtures of the mesogens were determined that would form mesophases at room temperature. The mesophases formed by the mixtures are shown in FIG. 1. By combining the optical textures of the liquid crystals in FIG. 1 with X-ray diffraction, the mesophases were identified. The X-ray diffraction patterns of the "A" and "B" series showed two sets of arc-shaped reflections that are perpendicular to each other—a pair of outer diffuse crescents corresponding to the intermolecular spacing, and a pair of inner crescents corresponding to the molecular layer spacing in the smectic phase. Dingemans, T. J., Murthy, S., and Samulski, E. T., *J. Phys. Chem. B*, 105, 8845 (2001). The layer spacing of the smectic "A" and "B" series was smaller than that of a smectic 4'-octyl-4-biphenyl-carbonitrile (8CB). However, the diffractograms of the "E" and "C" series possessed only the diffuse outer crescents that correspond to the translational period for the nematic phase. Liquid crystal "E" series is a class of apolar liquid crystals that usually exhibits lower viscosities than their polar counterparts. Petrzilka, M., *Mol. Cryst. Liq. Cryst.*, 111, 347 (1984). While the pure component 1-(4-ethyl-cyclohexyl)-4-[2-(4-pentyl-cyclohexyl)-ethyl]-benzene in the "E" series exhibited a smectic phase, its mixture with 1-ethyl-4-(4-pentyl-cyclohexyl)-benzene appeared to be nematic at ambient temperatures based on both the X-ray diffraction pattern and the liquid crystal texture (FIG. 1). Qian, X. M., Kuai, N. G., Hua, X., *Huadong Liqong Daxue XueBao*, 20, 688 (1994). Based on the X-ray diffraction pattern, the liquid crystal "C" series appeared to be nematic at ambient temperatures. The "C" series exhibited a broad range of mesophase(s) with a high clearing temperature reflecting the general trend that both the presence of a cyclohexyl ring and fluorine substitution on the aromatic rings increases the clearing temperature of the mesophase. Demus, D. D. (Editor), Gooby, J. W., Gray, G. W., Spiess, H. W. (Editor), PHYSICAL PROPERTIES OF LIQUID CRYSTALS (John Wiley & Sons) (1999).

Cell Attachment and Spreading Under Liquid Crystals

The viability of a living cell is reflected in a range of different dynamic processes, from macroscopic morphological variations to the molecular interactions inside different compartments of the cells. These processes include cell attachment and spreading on a surface, formation of focal adhesions, activation of protein signaling pathways, differentiation and proliferation. Of these phenomena, attachment has been shown to bias the viability of cells, and it is of prime importance for cell-based biotechnology. Chen, C. S., Mrksich, M., Huang, S., Whitesides, G. M., Ingber, D. E., *Science*, 276, 1425 (1997); Luk, Y. Y., Kato, M., Mrksich, M., *Langmuir*, 16, 9604 (2000).

Figure 2A:
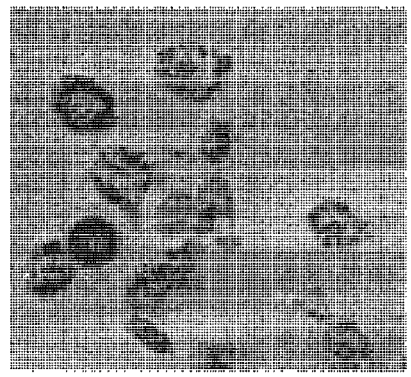
FIGS. 2A-2D are scanned images of optical micrographs of 3T3 fibroblasts immersed under liquid crystal 5CB (FIG. 2A); "C" Series (FIG. 2B); after "C" series is removed from the 3T3 fibroblasts (FIG. 2C); and under normal DMEM culture medium (FIG. 2D).
Figure 2B:
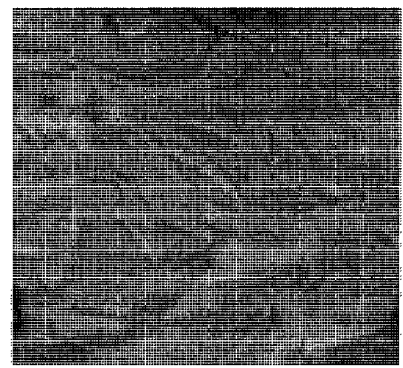
Figure 2C:
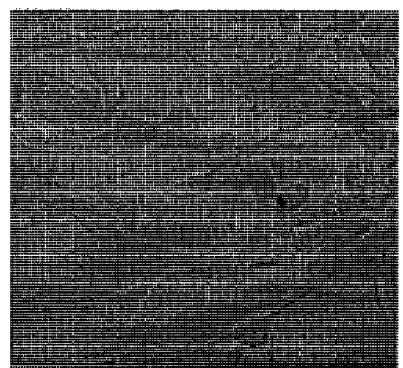
Figure 2D:
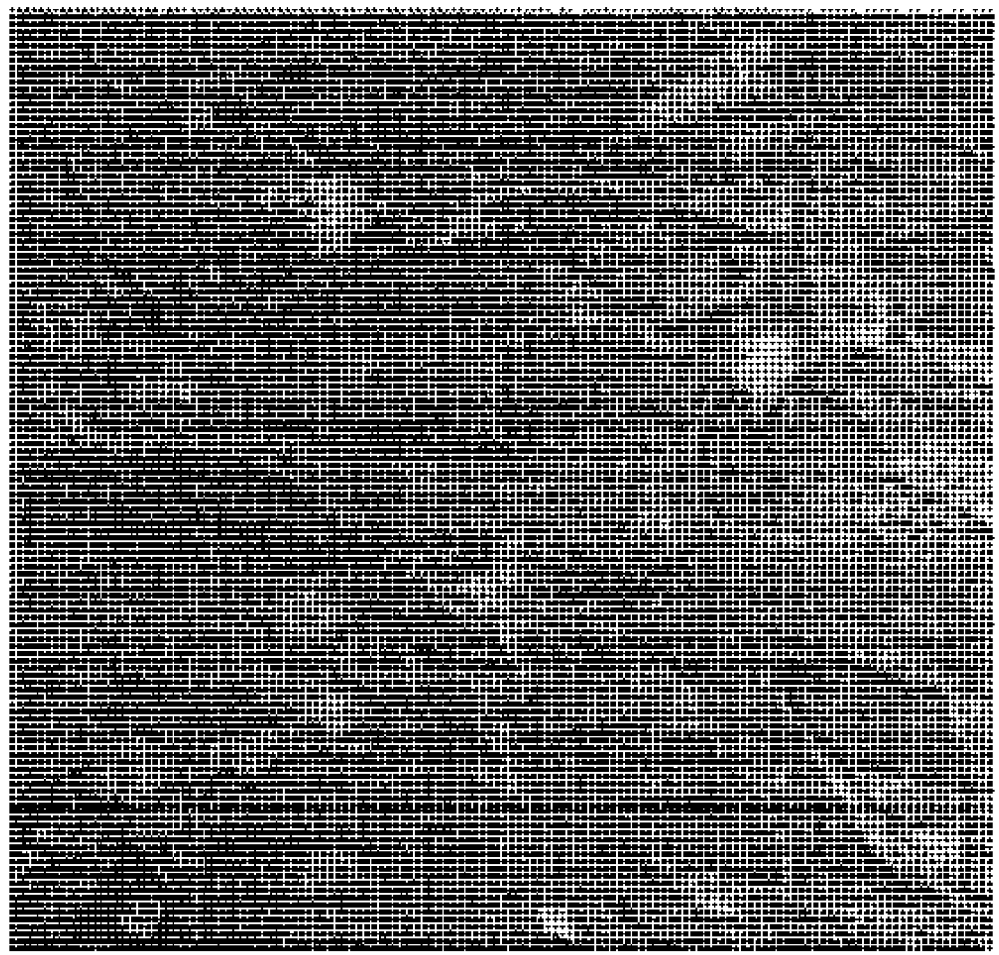

For adherent cells, the most basic requirement and evidence of a living cell is its attachment and adhesion to a surface. Most cells are adherent and mediated through a protein scaffold on surfaces. See Miranti C. K., Brugge, J. S., *Nat. Cell Biol.*, 4, E83 (2002); and Danen, E. H. J., Yamada, K. M., *J. Cell Physiol.*, 189, 1 (2001). The spreading of attached cells immersed under liquid crystals and immersed in normal culture medium (FIG. 2) was investigated. After plating the cells overnight in culture medium to obtain a confluent layer of cells, the medium was replaced with a layer of liquid crystal with a thickness of about 1 mm. The cells immersed under the liquid crystals were then further incubated for 4 to 8 hours. FIG. 2 shows a comparison between the morphology of the plated 3T3 fibroblast cells under 5CB (FIG. 2A), under the "C" series (FIG. 2B), after the "C" series was removed from the plated cells (FIG. 2C), and cells cultured with normal culture medium (FIG. 2D). Inspection of FIG. 2 show that cells immersed under 5CB bulge up or "round up" whereas cells under the "C" series spread to an extent that is indistinguishable from cells under normal culture medium. The low resolution of the images of the cells under the liquid crystals was caused by birefringence of the liquid crystals. Following the removal of "C" series liquid crystals from contact with the cells, details of the morphology of the spread cells such as lamellipodia and the presence of the nucleus were indistinguishable from normal healthy living cells. On the other hand, upon removal of 5CB, rounded up 3T3 fibroblasts were observed, and many were displaced from the surface by rinsing. Various factors may cause the rounding up of a cell from a spread morphology, one of which is cell death. From this experiment, 5CB stresses and harms plated cells, and may cause cell death. Furthermore, "C" series liquid crystals are appropriate for use in applications where living cells are to be investigated.

Fluorescent Imaging of the Viability of Cells Treated with Liquid Crystals

Figure 3:
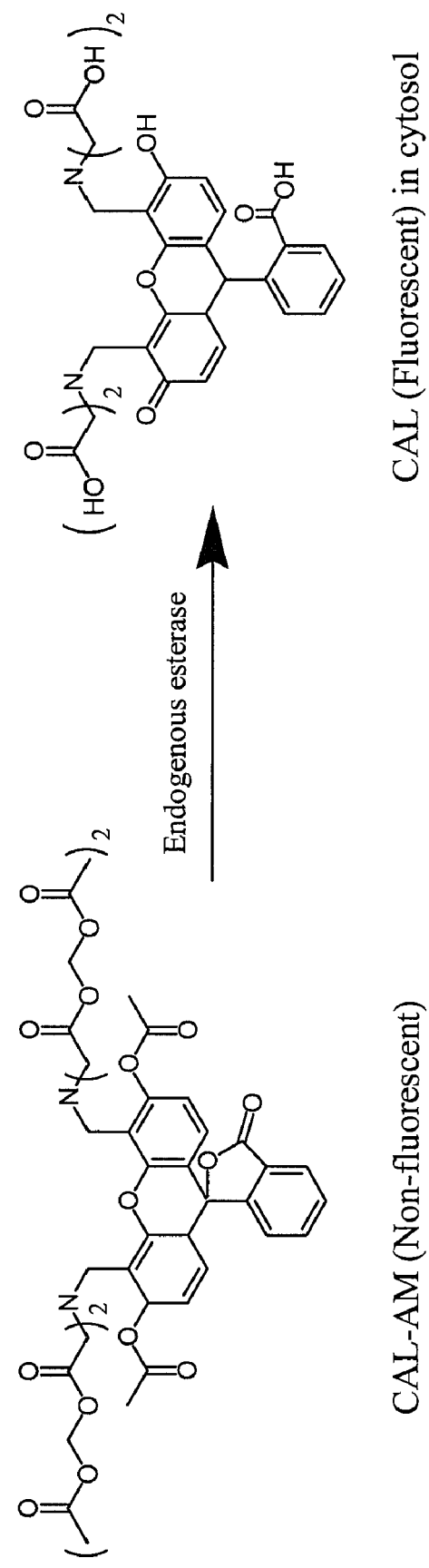
FIG. 3 depicts a hydrolysis reaction of the non-fluorescent CAL-AM by endogenous esterase in cytosol to afford the green fluorescent CAL in cells.

To quantify the viability of cells treated with liquid crystals, viability/cytotoxicity assays were conducted. The viability assay utilized the fluorescent precursor calcein acetoxymethylester (CAL-AM), which is permeable to the membrane of cells. Upon entering the cells, CAL-AM is a substrate for the endogenous esterase that can hydrolyze CAL-AM to afford a green fluorescent product—Calcein (CAL)—in the cytosol (FIG. 3). Hence, the presence of green fluorescence from CAL in cells is evidence of the esterase activity as well as an intact membrane that retains the esterase products in the cells. Both of these are indicators of living cells.

By measuring the level of intensity of CAL fluorescence in cells treated with different liquid crystals relative to that measured without treatment with liquid crystal (in culture medium), the effect of eight liquid crystals upon the viability of 3T3 fibroblast and SV-40 HCEC cells was quantified. A high relative fluorescence indicated that the treatment with liquid crystal had minimal effect on the viability of cells whereas a low relative fluorescence indicated a high death rate of cells due to exposure to liquid crystal.

Figure 4:
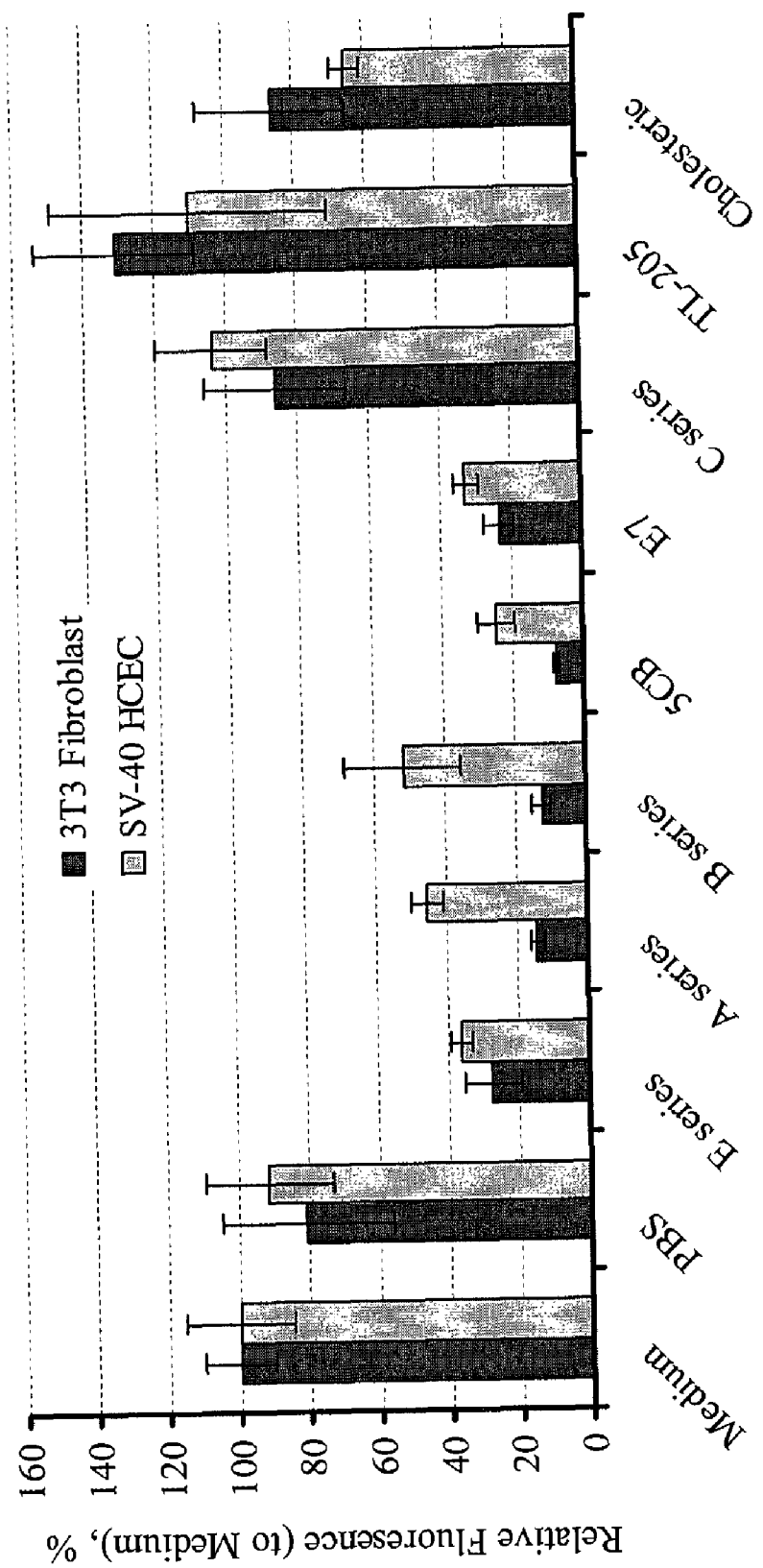
FIG. 4 is a graph depicting cell viability after treatment with liquid crystals. The relative intensities of the fluorescence from CAL in 3T3 fibroblasts (black bars) and in SV-40 HCEC (gray bars) are plotted for each liquid crystal treatment (4 hours, 10,000 cells/well, 6 wells/treatment).

FIG. 4 shows the relative fluorescence of CAL in cells treated with liquid crystals. In general, the liquid crystals showed similar effects on the viability of 3T3 fibroblasts and SV-40 HCECs. Before discussing the effects of the liquid crystal on cells, it is noted that a control experiment in which liquid crystal was replaced with pure PBS buffer did not cause a significant decrease in the relative fluorescence of CAL in cells. This result was significant because it demonstrated that the short-term starvation due to the removal of the nutrients did not affect the viability of cells in the experimental setup. Hence, any effect on cells due to the treatment of the liquid crystal may be largely attributed to the chemical/toxic effect of the specific liquid crystal. Inspection of FIG. 4 reveals that "E" series, "A" series, and "B" series, 5CB, and E7 are all toxic to both 3T3 fibroblast and SV-40 HCEC. Treatment of the cells with these five liquid crystals caused the CAL fluorescence to decrease to less than 30% for 3T3 fibroblast, and to less than 50% for SV-40 HCEC. However, treatment of both cell lines with the "C" series and TL 205 led to levels of CAL fluorescence that were similar to the CAL fluorescence measured with cells not treated with liquid crystals (both culture medium and pure PBS buffer). Therefore, these two liquid crystals exhibit little to no toxicity. Finally, the cholesteric series exhibited only mild toxicity towards both cell lines investigated. For these reasons, "C" series liquid crystals, TL205, and cholesteric liquid crystals are all useful in applications where liquid crystals are to be used in contact with liquid crystals.

Figure 5A:
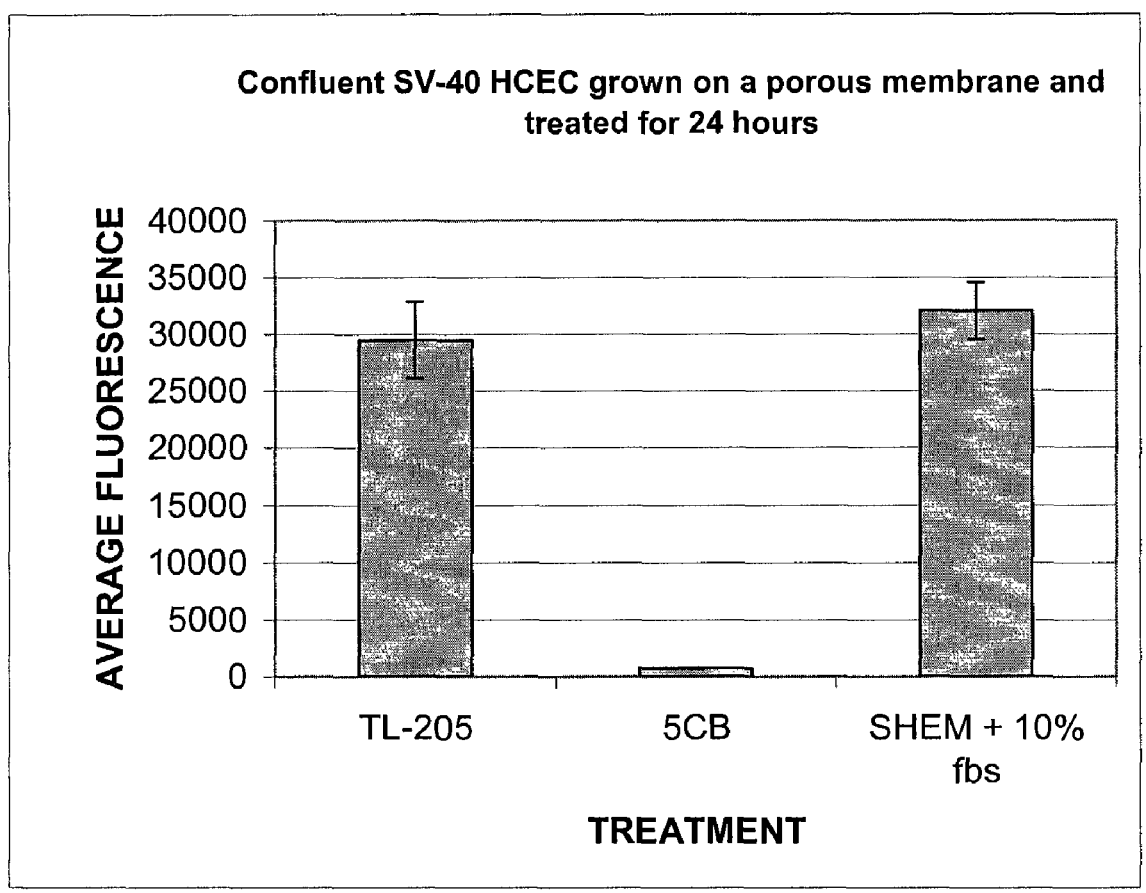
FIGS. 5A and 5B are graphs depicting cell viability following prolonged exposure to TL-205 and 5CB.
Figure 5B:
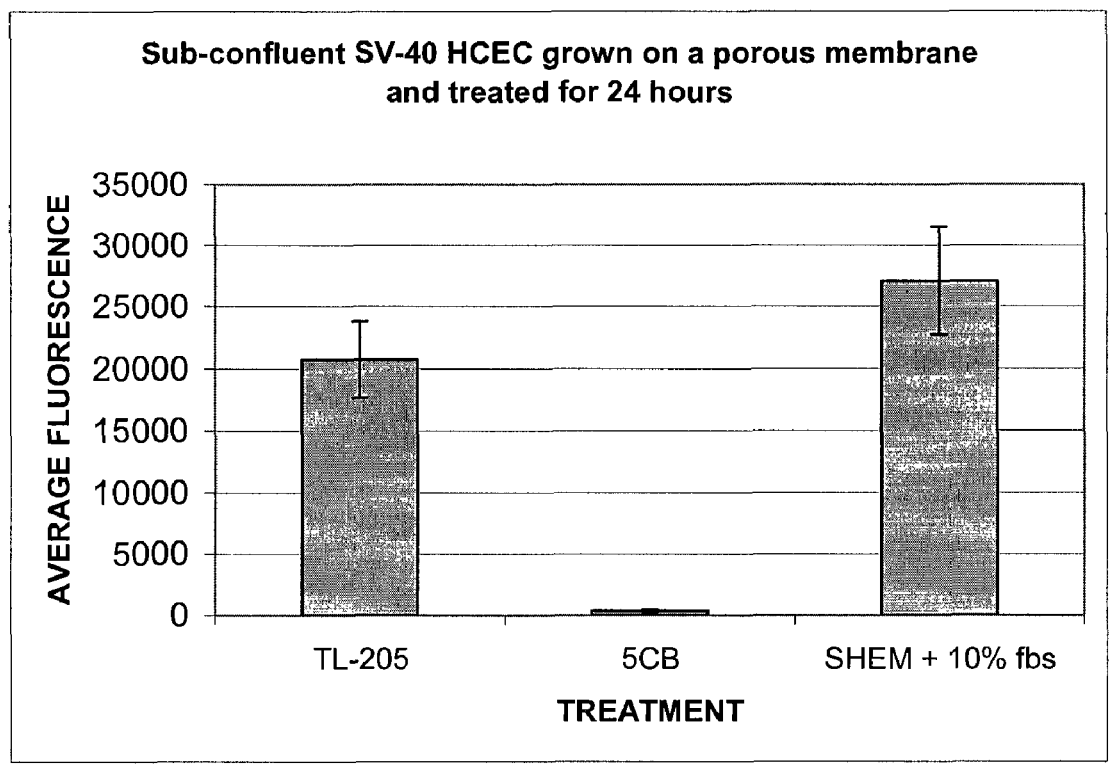

FIGS. 5A and 5B present the results of additional experiments to evaluate the toxicity of two different liquid crystals, 5CB and TL-205, following prolonged exposure to cells. For these experiments, TRANSWELL assays were carried out in which cell cultures were plated onto membranes in a TRANSWELL plate such that they were fed from below by liquid media while in continual contact with the liquid crystal, which was directly overlaid on the cells themselves. Briefly, SV-40 human corneal epithelial cells (HCEC) were grown in SHEM+10% fetal bovine serum. Cells were removed from T-75 tissue culture plates via trypsinization, and counted using a hemacytometer. Cells were plated onto TRANSWELL membranes (3 μm pore size, Corning, Inc., Corning, N.Y.) that allowed them to remain in contact with the liquid crystal as well as with the growth medium for 24 hours. Cells were plated at a concentration of 20,000 cells/well and allowed to grow. Some cells were tested at a density of confluence, approximately 45,000 cells (FIG. 5A), while another set was tested at a density of sub-confluence, approximately 30,000 cells/well (FIG. 5B). Cells were treated with 50 μL of either media, TL-205, or 5CB in the upper chamber of the TRANSWELL, while the lower chamber received 180 μL of SHEM. The incubation time was 24 hours. The cells were then rinsed three times to remove media, TL-205, or 5CB. Calcein-AM was added to each well, and the cell fluorescence was measured to assess cell number. Fluorescence was read using a SYNERGY HT plate reader (Bio-Tek, Instruments, Inc., Winooksi, Vt.). The results of these toxicity evaluations are consistent with the results presented in FIG. 4 and indicate that prolonged exposure of either type of cells to 5CB appears to kill cells while exposure to TL-205 does not.

Figure 6A:
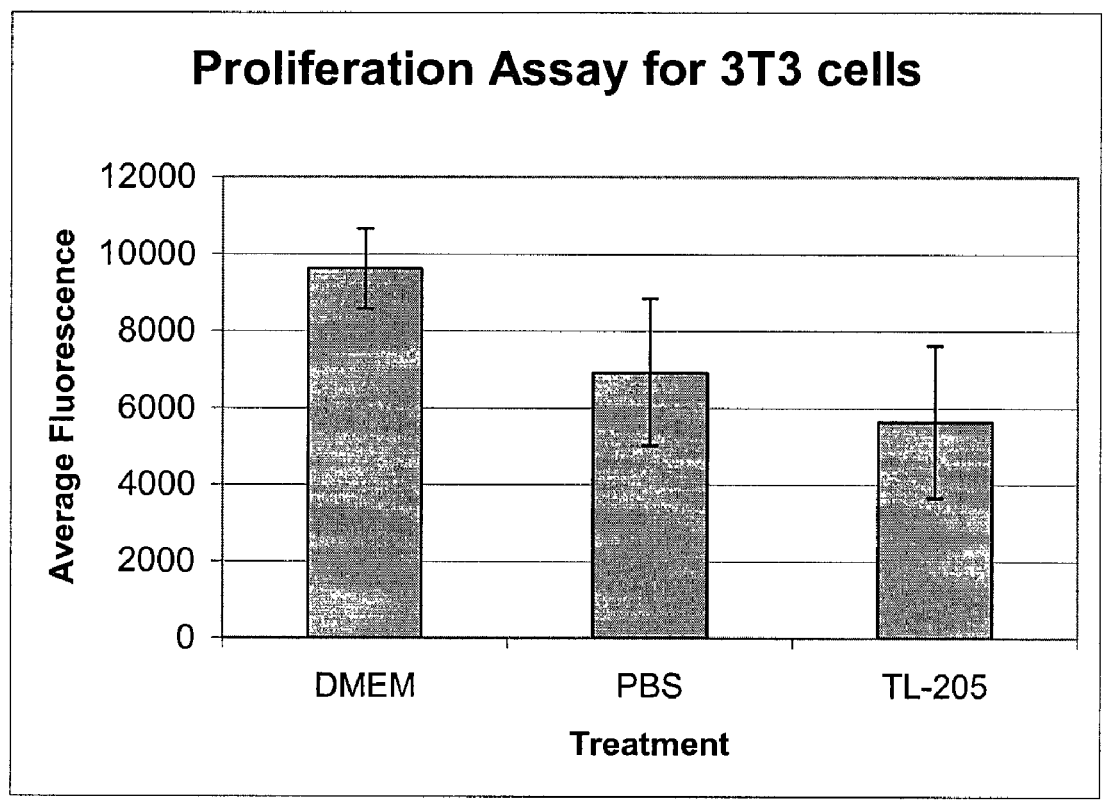
FIGS. 6A and 6B are graphs depicting the ability of cells to proliferate following prolonged exposure to TL-205.
Figure 6B:
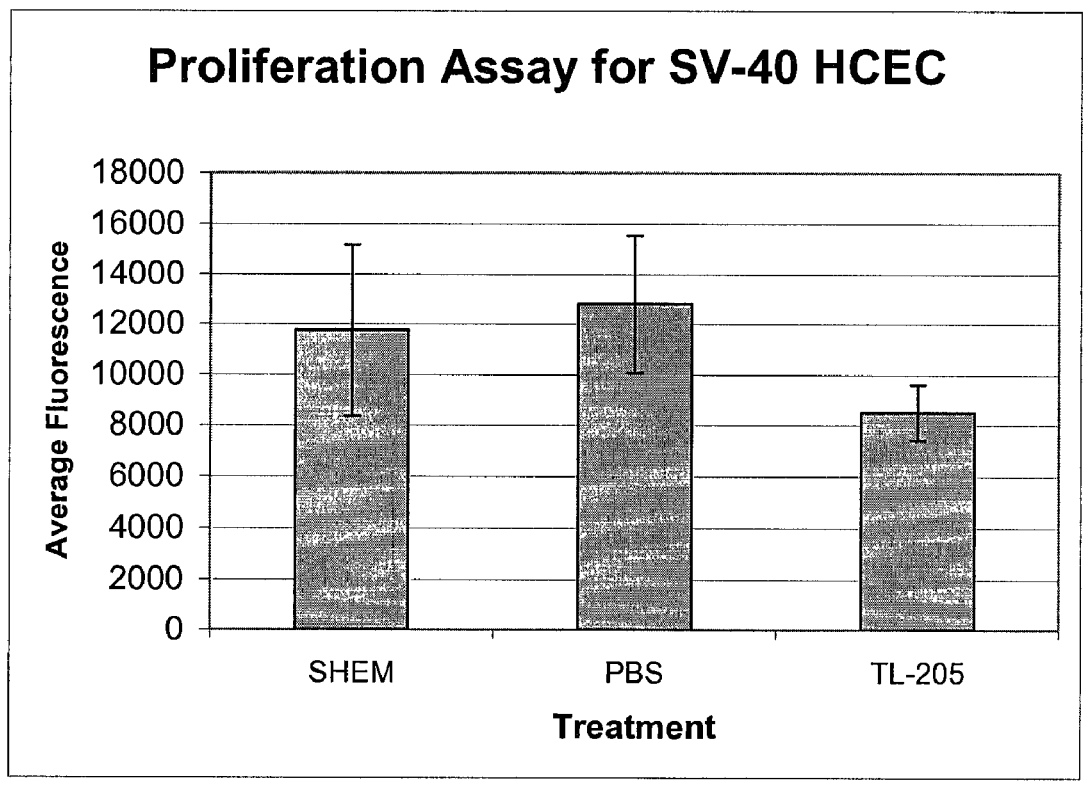

Further experiments were carried out to evaluate the ability of the cells exposed to TL-205 to proliferate following the 24 hour incubation period. FIG. 6 shows that cells in direct contact with TL-205 remain viable for prolonged periods and do not appear to be significantly different from control cells exposed to PBS. In this experiment, two cell types were tested on TRANSWELL membranes that allowed them to remain in contact with the liquid crystal as well as with the growth medium for 24 hours. SV-40 HCEC cells were grown in SHEM+10% fetal bovine serum (FIG. 5B); NIH 3T3 fibroblasts were grown in DMEM+10% calf serum (FIG. 5A). Cells were removed from T-75 culture plates by trypsinization, counted using a hemacytometer, and plated onto TRANSWELL membranes at a concentration of 5000 cells/well and allowed to attach for 18 hours in an incubator (37° C. and 5% $CO_2$). Following incubation, cells were treated with 50 µL of either media, PBS, or TL-205 for 24 hours. The lower chamber of the TRANSWELL received 180 µL of media. The cells were then rinsed three times with PBS to remove the media, PBS, or TL-205. Media+10% serum was added (50 µL to the upper chamber and 200 µL to the lower chamber), and the cells were allowed to proliferate for 5 days. After the five day growth period, Calcein-AM was added and the cell fluorescence was measured to assess cell number and read using a SYNERGY HT plate reader (Bio-Tek, Instruments, Inc., Winooksi, Vt.), as described (supra).

For the purposes of this invention, a liquid crystal that exhibits reduced toxicity to cells is generally a liquid crystal or mixture of liquid crystals in which the CAL fluorescence of 3T3 fibroblast cells treated with the liquid crystal or mixture of liquid crystals for four hours as described herein is at least 60 percent, is more preferably at least 70 percent, or is still more preferably at least 80 percent, at least 90 percent, or at least 95 percent, relative to similar cells which were not treated with the liquid crystal or mixture of liquid crystals. In some particular applications, this definition can be altered to correlate to the specific cell that the liquid crystal is to be used with using the particular cell type in the analysis in place of 3T3 fibroblast cells.

Chemically Inert Fluorophenyl Liquid Crystals and Cell Immunity

Table 2 shows that the "C" series of liquid crystals and TL205 possess fluorinated phenyl and fluorinated cyclohexyl functional groups, whereas 5CB and E7 both include cyano groups (Table 2). Interestingly, both the "C" series of liquid crystals and TL205 do not cause a reduction in the CAL fluorescence in 3T3 fibroblasts and SV-40 HCEC, whereas both 5CB and E7 exhibit toxicity to both cell lines. It was thus concluded that functional groups on the liquid crystals are an important factor in determining the viability/cytotoxicity effects of liquid crystals on cells. On the other hand, physical properties of liquid crystals such as viscosity and clearing temperature did not appear to serve as useful indicators of toxicity of liquid crystals towards cells. It is noted that 5CB is an isotropic liquid at 37° C. whereas E7 is nematic. It is further noted that the "E" series was found to be toxic to both cell lines. Because the "E" series is comprised of olefins that have no special functional groups such as fluorine, it is hypothesized that the inertness observed for the "C" series and TL205 is associated with the presence of fluorinated phenyl and cycloalkyl groups on these liquid crystals. Thus, liquid crystals that include fluorine atoms, fluorophenyl groups, and fluorinated cyclohexyl groups are suitable for employment in application where cells will contact liquid crystals. TL205 and its individual liquid crystal compound components is a suitable liquid crystal with low toxicity that may be used in cell culture media of the invention. The two difluorophenyl compounds that make up the "C" series mixture are also suitable liquid crystal compounds with low toxicity that may be used in cell culture media of the invention. The same is true for the cholesteric liquid crystal mixture components.

Liquid crystals that include fluorophenyl groups have been widely investigated for use in display technology based on liquid crystals. Kirsch, P., Bremer, M., *Angew. Chem., Int. Ed.,* 39, 4216 (2000); Takeshi, I., ORGANOFLUORINE CHEMISTRY: PRINCIPLES AND COMMERCIAL APPLICATIONS; Banks, R. E., Smart, B. E., Tatlow, J. C., Eds., (Plenum Press: New York), p. 263 (1994); Guittard, F., De Givenchy, E. T., Geribaidi, S., Carnbon, A., *J. Fluorine Chem.,* 100, 85 (1999). Fluorine substitution of the aromatic rings leads to many unique molecular properties that cannot be realized with other functional groups. First, the small size of fluorine provides minimal steric disruption of molecular packing in liquid crystals. Hence, the effect of the fluorine-substitution is largely electronic. Second, the large electronegativity of the fluorine atom leads to a strong polarization in the C—F bond and induces a strong local dipole moment. Third, the aromatic ring bears a subtle but important quadrupole moment that contributes significantly in binding and intermolecular interactions. Ma, J. C., Dougherty, D. A., *Chem. Rev.,* 97, 1303 (1997). Because of the aromaticity of the 7T electrons, a partial negative charge is localized above and below the a skeleton of the cyclic ring, compensated by the partial positive charge of the hydrogen equatorial to the ring. This unique distribution of partial charges gives rise to a quadrupole moment in the aromatic ring consisting of a "tail-to-tail" alignment of two dipoles perpendicular to either side of the facet of the aromatic ring. Dougherty, D. A., *Science,* 271, 163 (1996). However, both the magnitude and sign of this quadrupole moment can be changed and reversed by substituting electronegative atoms in place of the equatorial hydrogen atoms on the aromatic ring. Mecozzi, S., West A. P., Dougherty, D. A., P. *Natl. Acad. Sci. USA* 93, 10566 (1996). The highly electron withdrawing nature of fluorine substitution on the phenyl ring reduces the electron density in the aromatic rings, thus leading to a large reduction in the quadrupole moment of the aromatic ring. West, A. P., Mecozzi, S., Dougherty, D. A., *J. Phys. Org. Chem.,* 10, 347 (1997); Waters, M. L., *Curr. Opin. Chem. Biol.,* 6, 736 (2002). Therefore, unlike the case where perfluorinated aliphatic chains repel non-fluorinated aliphatic chains, fluorinated aromatic rings attract non-fluorinated aromatics. Weck, M., Dunn, A. R., Matsumoto, K., Coates, G. W., Lob-Kovsky, E. B., Grubb, R. H., *Angew. Chem., Int Ed.* 38, 2741 (1999). Without being bound to theory, the above-described unique characteristics of this class of mesogens may play a significant role in the chemical inertness of fluorophenyl substituted liquid crystals when contacting them with cells.

Finally it is noted that a small increase in the CAL fluorescence was observed for cells treated with fluorophenyl and fluorocyclohexyl mesogens. The experiments were repeated for both cell lines, and the increase in the CAL fluorescence was confirmed for both cell lines. Perfluorinated alkyl chains used in artificial blood have an exceptionally large capacity for solvating oxygen and carbon dioxide. Hill, S. E., Can. J.

*Anaesth.*, 48, 532 (2001). While the mechanism for dissolving oxygen is different from hemoglobin, oxygen-deprived tissues can easily extract this readily dissolved oxygen. Teicher B. "Use of Perfluorocarbon Emulsions in Cancer Therapy", Chang T. M. S., ed. BLOOD SUBSTITUTES AND OXYGEN CARRIERS, (New York: Marcel Dekker), p. 640 (1993). It is hypothesized that fluorinated liquid crystal molecules may cause a change in cellular metabolism such that intracellular esterase activity is upregulated.

In summary, the effects of eight liquid crystals with unique sets of functional groups on the viability of two mammalian cell lines immersed in the liquid crystals was investigated. The chemical functional groups on the liquid crystals was found to be related to the toxicity of the liquid crystal with respect to the cell. A general and specific set of functional groups was identified that, when incorporated in mesogens, reduce toxicity to cells. The exact mechanism by which these functional groups define liquid crystal-cell interactions and thus toxicity, in general, is not completely understood, but the reduced toxicity of certain liquid crystal compositions makes these compositions useful in a wide array of applications, particularly those where the liquid crystals will contact cells.

Bio-Inert Non-Amphiphilic Lyotropic Liquid Crystals

Experiments were conducted to evaluate the biocompatibility of another class of liquid crystals. In particular, the experiments were designed to test whether several different types of biological interactions could be carried out in the presence of substantially aqueous, non-amphiphilic lyotropic liquid crystals. The lyotropic liquid crystals were designed and selected according to four criteria. First, the lyotropic liquid crystals were substantially aqueous. Second, the lyotropic liquid crystals possessed anisotropic optical properties. Third, biomolecules could be dissolved in the lyotropic liquid crystals and still retain their specific binding or enzymatic activity. This characteristic optimizes detection of biomolecular interactions within liquid crystals. Fourth, the viscosity of the lyotropic liquid crystal was not high.

For a surface-based assay using lyotropic liquid crystals, the surface optimally possesses certain properties. Among these is the property of the surface to align the lyotropic liquid crystal in orientations that are distinguishable in the absence and presence of the biomolecular interaction. Another important surface characteristic is its ability to resist non-specific adsorption of biomolecules in order to detect a specific binding event.

In the experiments described below, surfaces were assembled to comprise self-assembled monolayers (SAMS) of alkanethiols on gold that resists the non-specific adsorption of proteins. These experiments demonstrate that this class of hydrophilic SAMs can align lyotropic liquid crystals with controlled azimuthal direction.

Test of Antibody Binding in the Liquid Crystals

Lyotropic liquid crystals were investigated for their biocompatibility and bio-inertness based on the following three criteria: (1) viscosity; (2) observed birefringence of the liquid crystal; and (3) protein binding activity when proteins are dissolved in the lyotropic liquid crystals. The stability of protein structure in the lyotropic liquid crystals is implicitly tested based on the evaluation of criterion (3). The binding activity of antibodies in the liquid crystal was tested by covalent attachment of an antibody to a solid surface and measurement of the binding of a fluorescently labeled antibody to the immobilized antibody.

Modification of the glass surface is accomplished by reaction of an alkoxy group of a (trialkoxysilyl)alkyl isocyanate such as, but not limited to, $(R^aO)_3Si-(CH_2)_n-N=C=O$ wherein $R^a$ is a straight or branched chain alkyl group having 1 to 6 carbon atoms and s is an integer having a value of from 2 to 6. In some embodiments, $R^a$ is a methyl, ethyl, or propyl group, and s is 3. Alkoxy groups in such compounds are typically methoxy, ethoxy, propoxy, pentoxy, or hexoxy groups whereas the alkyl groups in such compounds are typically ethyl, propyl, butyl, pentyl, or hexyl groups. For example, glass surfaces were modified using 3-(triethoxysilyl)propyl isocyanate by treating the glass with the (trialkoxysilyl)alkyl isocyanate (glass slides were soaked in toluene solutions of the isocyanate for 12 hours at 40° C.) affording a glass surface with isocyanate groups for reaction with other compounds. The concentration of 3-(triethoxysilyl)propyl isocyanate was 3% w/v. The modified glass surfaces were rinsed with toluene, hexane and ether, and dried thoroughly with a stream of nitrogen.

After the glass surfaces were modified, proteins were immobilized on the modified surfaces by reacting a lysine residue of the protein with the isocyanates on the surfaces at room temperature. Protein immobilization, as illustrated in Scheme 1, is essentially traceless in that it does not result in the production of byproducts. A similar scheme has been used to modify proteins with a fluorescent tag. Chia, S. Y.; Cao, J. G.; Stoddart, J. F.; Zink, J. I. *Angewandte Chemie-International Edition* 2001, 40, 2447.

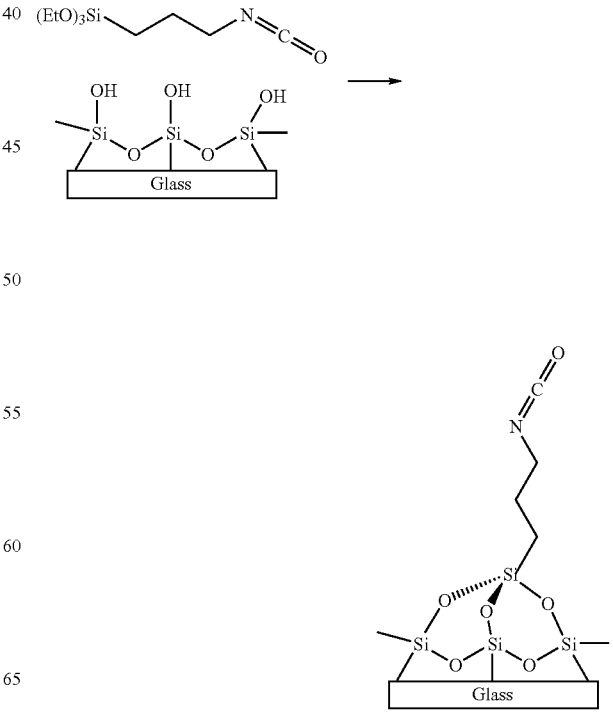

Scheme 1. Attachment of Biomolecules to Glass Surfaces

-continued

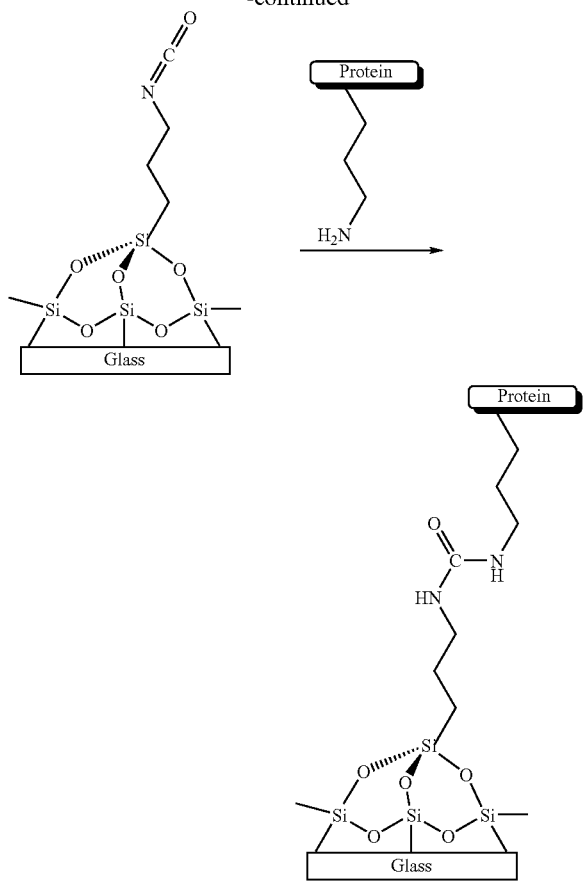

Figure 15:
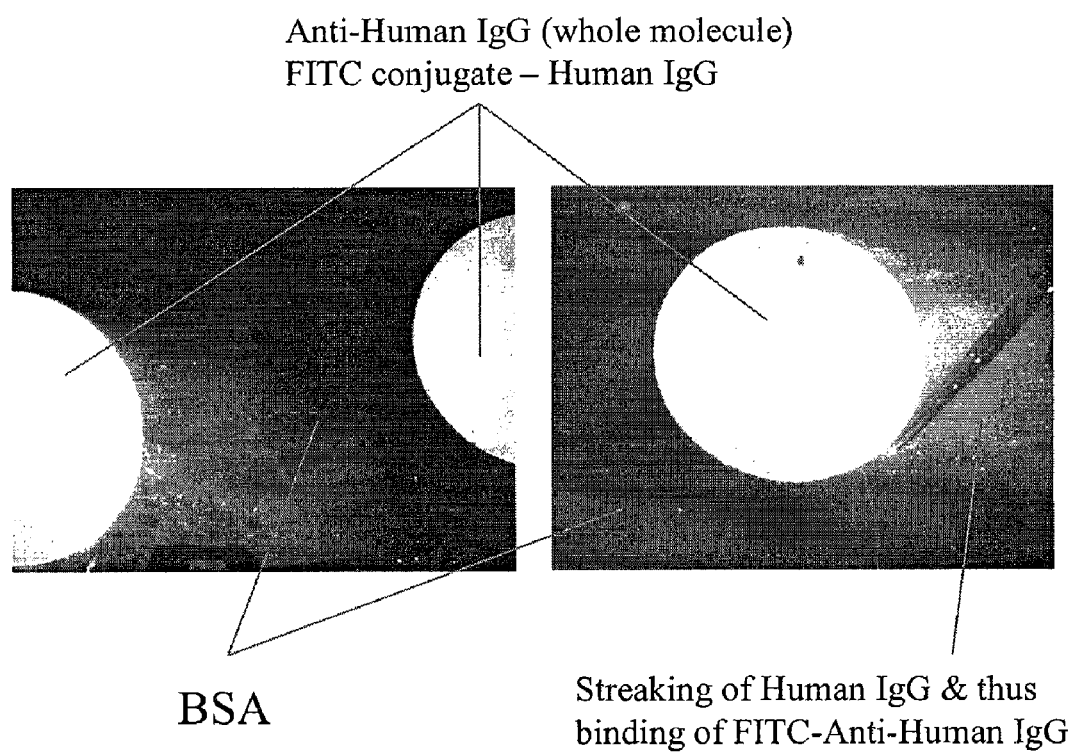
FIG. 15 is a scanned image of a glass slide examined using a fluorescent microscope showing that FITC fluorescence was only found in the arrayed spots, indicating that there was no non-specific adsorption of FITC conjugated anti-human IgG on the surfaces.
Figure 16:
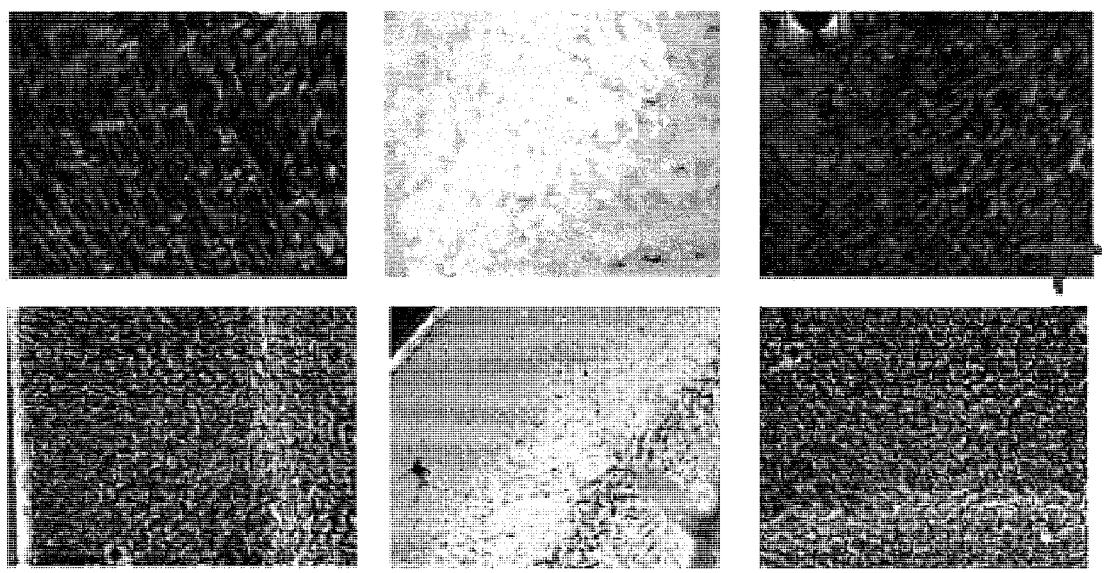
FIG. 16 is a scanned image showing alignment of 15 wt % DSCG in pure water sandwiched between two surfaces presenting SAMs of $HO(CH_2CH_2O)_3(CH_2)_{11}S$ on obliquely deposited gold surfaces (45° from normal) shown at 10× and 4× magnification.
Figure 17:
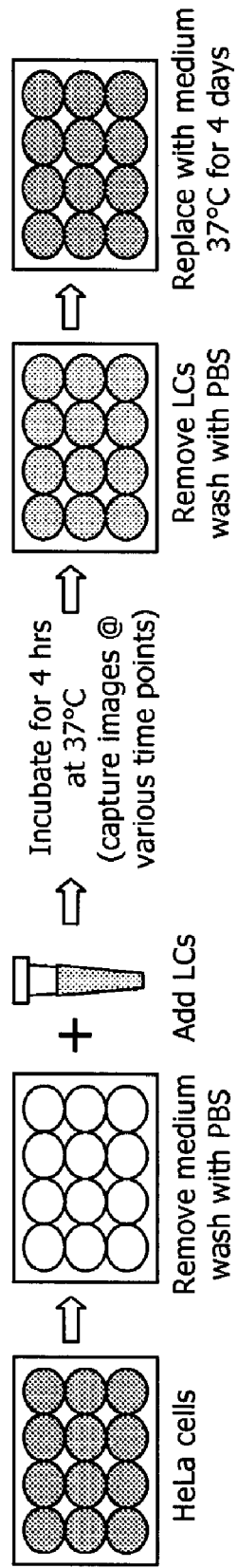
FIG. 17 is a schematic illustration of the effect of liquid crystals on cells.
Figure 18:
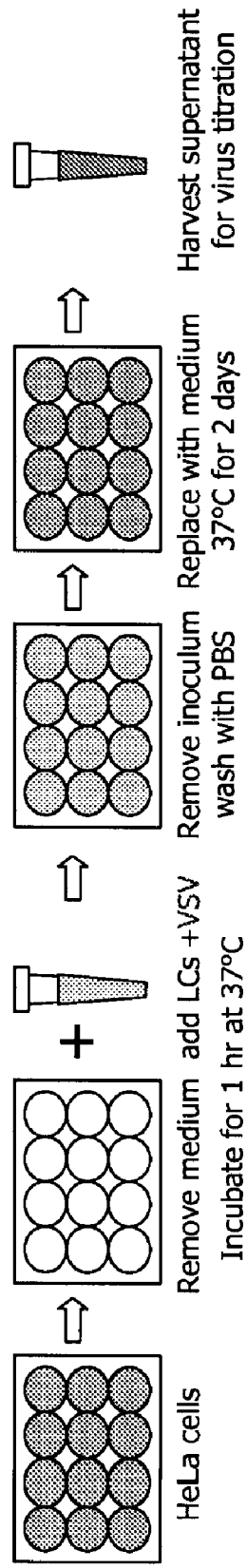
FIG. 18 is a schematic illustration of the effect of liquid crystals when a virus is inoculated to cells.
Figure 19:
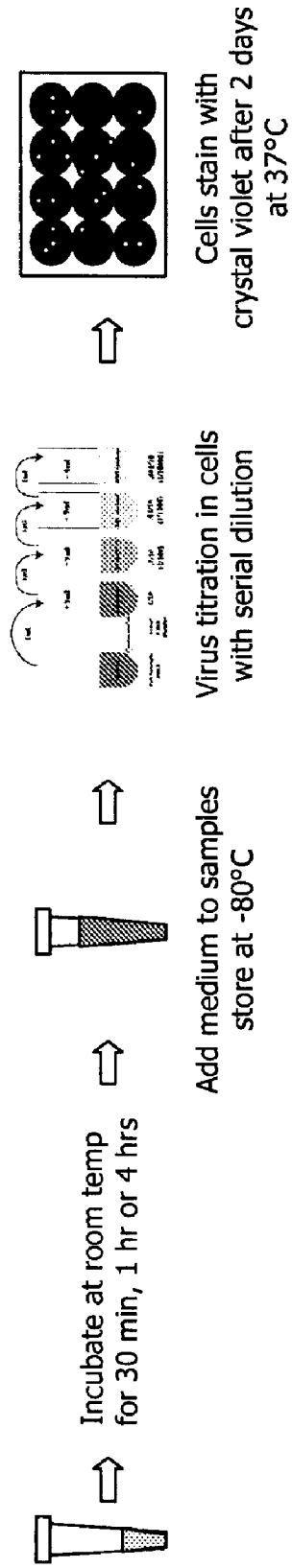
FIG. 19 is a schematic illustration of the effect of liquid crystals on virus infectivity.
Figure 20:
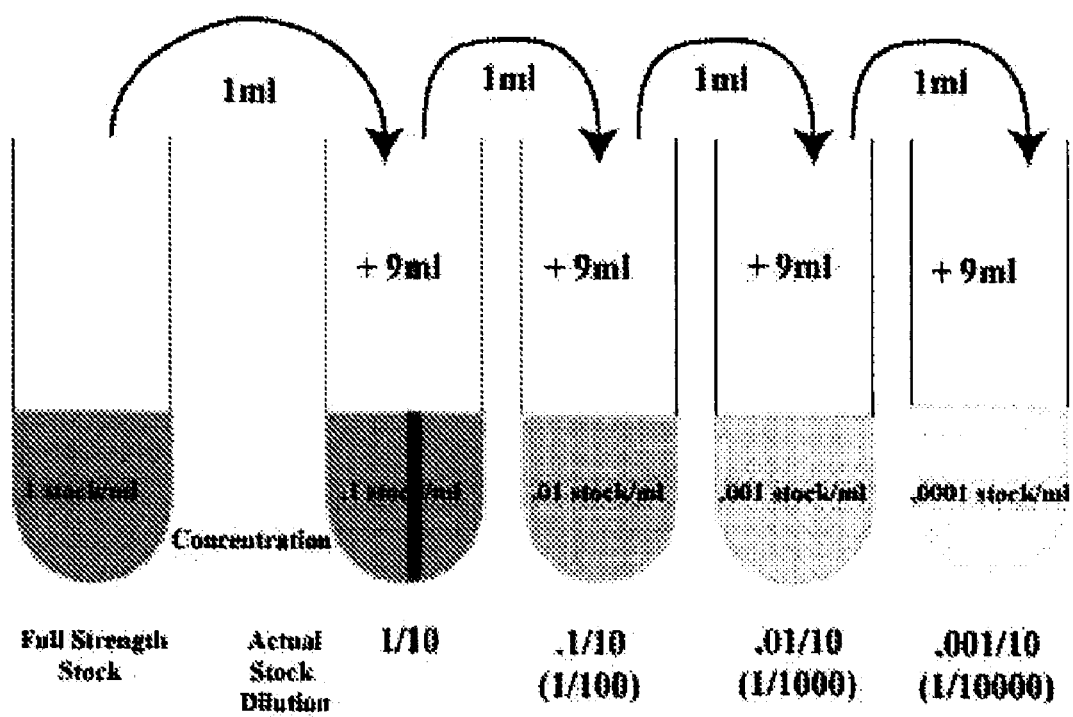
FIG. 20 is a schematic illustration of the enlargement of virus titration in cells with serial dilution.

In this example, microliter droplets of a solution containing 4 μM Human IgG were applied to an isocyanate-modified glass surface. The glass surface was incubated at room temperature in a covered Petri dish containing cottons wet with water to keep a constant moisturized environment. The resulting surface was then rinsed thoroughly with 1×PBS buffer (pH 7.4). A solution of BSA (1 mg/mL) was applied to cover the whole surface for 2 hours. BSA and other serum albumins may be used to form surfaces that resist non-specific adsorption of biomolecules that do not bind to a receptor bound to the surface. The surface was then rinsed thoroughly with PBS buffer. A solution of 200 nM anti-Human IgG (whole molecule) conjugated with FITC in 10% DSCG liquid crystal was applied to cover the whole surface for 4 hours at room temperature, followed by rinsing with PBS and pure water. Other biomolecules that may be used in accordance with the invention include, but are not limited to, peptides, polypeptides, DNA, RNA, DNA fragments, RNA fragments, cells, viruses, and bacteria. The slides were examined under a fluorescent microscope to evaluate localization of fluorescent signal. As shown in FIG. 15, FITC fluorescence was only found in the arrayed spots, indicating that there was no non-specific adsorption of FITC conjugated anti-human IgG (whole molecule) on the surfaces. Hence, these results show the specificity between the binding of FITC conjugated anti-human IgG (in lyotropic liquid crystal) and Human IgG versus BSA. This result also implicitly demonstrates that the extent of denaturation of anti-human IgG in DSCG lyotropic liquid crystal was minimal or at least not sufficient to interfere the binding with antigens. These results together show that (1) lyotropic liquid crystals based on zwitterionic surfactant (tetradecyldimethylamineoxide) preserve specific antibody binding activity; (2) lyotropic liquid crystals based on Brij, Triton, CsPFO and laurate system all interfered with antibody binding activities. This observation may be due to effects of high viscosity on binding kinetics, such that the more viscous liquid crystals (e.g. Brij, Triton, CsPFO and laurate system) result in slow binding kinetics. Another possible factor may be denaturation of the protein or the antibody in the presence of some liquid crystals.

In addition to the above, a formulation to expand the nematic temperature range of chromonic lyotropic liquid crystals, such as DSCG, was developed. By adding a small amount of non-ionic surfactant, the clearing temperature for DSCG was increased. For example, at 9% (by weight) DSCG is isotropic at 23° C. By adding 7% by weight Triton X114, the nematic phase was observed at 23° C. for 8.36 wt % DSCG.

The following table provides relevant characteristics for several lyotropic liquid crystals.

| Property | DSCG 9% wt | Triton 60% wt | Brij 50% wt | AMO 20% wt | CsPFO | Laurate |
|---|---|---|---|---|---|---|
| Birefringence | 0.1-0.3 | 0.005-0.1 | 0.005-0.1 | 0.005-0.1 | 0.01-0.1 | 0.05-0.15 |
| Alignment | Good | Medium | Medium | Medium | Medium | Medium |
| Viscosity(cp) | 0.5-30 | >100 | >100 | 50-200 | 1-100 | 1-100 |
| Protein Binding | + | − | − | + | − | − |

Surfaces that Orient Liquid Crystals

A second element of the some combinations of LCs and lyotropic liquid crystals relates to surfaces that orient the lyotropic LCs. In this example, the alignment of the chromolyn-based liquid crystal shown below in which $R^1=R^2=COOH$ was investigated on surfaces with SAMs comprising alkanethiols supported on obliquely deposited gold films.

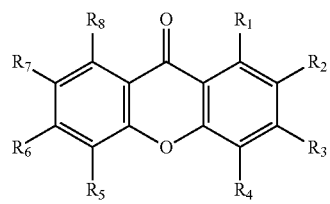

-continued

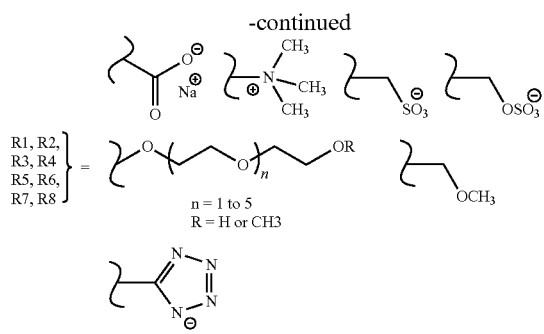

The binding of antibodies dissolved in the chromolyn lyotropic liquid crystal shown above to antigens covalently immobilized on a glass substrate was further investigated. The liquid crystal images shown in FIG. 16 show that 15% wt DSCG in pure water was uniformly aligned on self-assembled monolayers formed from alkanethiols [HO $(CH_2CH_2O)_3(CH_2)_{11}SH$] supported on metallized surfaces such as obliquely deposited gold films (45° from normal). Other thiols that may be used include, but are not limited to, compounds of formula HS—$(CH_2)_p$—$(OCH_2CH_2)_q$—OH, where p is an integer with a value of from 5 to 20 and q is an integer with a value of from 1 to 6. In some embodiments, p is 11 and q is 3 or 4. Furthermore, this class of liquid crystal exhibits a nematic phase over a wide range of weight percentage (3 wt % to 15 wt %), which shows low viscosity. The observed birefringence as evident from FIG. 15, was very high, and qualitatively higher than all other lyotropic liquid crystals known. This result demonstrates that the azimuthal direction of the uniform alignment of lyotropic liquid crystal DSCG is sensitive to molecular details of the SAMs on obliquely deposited gold films. This provides evidence of the high level of control of the alignment of liquid crystals.

It is further possible to inspect the optical appearance of the bulk liquid crystal to detect antibody-antigen interactions in solution, i.e. where neither the antibody nor its antigen are bound to the surface. In this case, VSV is detected by inspecting the optical appearance of the bulk liquid crystal DSCG in the presence of anti-VSV antibody supplied in solution. Briefly, lyotropic liquid crystals based on disodium chromoglycate (DSCG) are prepared as two binary systems by mixing 15 wt % DSCG and 85 wt % water, and aging the solution for 12 hours for complete solubility and homogeneity of DSCG prior to use.

For the VSV samples, the supernatant from virus-infected HeLa cells is collected and purified as followed. Briefly, a crude virus particle pellet is obtained after cell debris are removed from the supernatant and centrifuged through a 30% sucrose (w/v) cushion in STE buffer (10 mM Tris-NaCl, 0.1 M NaCl, 1 mM EDTA, pH of 8.0). The pellet is resuspended in STE buffer and subjected to further purification through a buoyant density gradient (20% to 70% of sucrose in STE buffer) and centrifuged for 18 hours in a Beckman SW41 rotor at 120,000 g at 4° C. After fractionation of the gradient, the virus fractions are collected and later confirmed by virus titration and immunoassay with anti-VSV antibodies. The virus particles are then concentrated by pelleting through another 30% sucrose (w/v) cushion and resuspended in STE buffer. This solution is stored at −80° C. in working aliquots until needed. The titer of infectious virus particles in solution is determined by means of a plaque assay, and is calculated according to the relation where the titer is given in plaque forming units per milliliter (pfu/mL). For the control solutions, samples are prepared using the same procedure described above except that supernatant from mock-infected HeLa cells is used. Roughly equal numbers of cells are used to produce the virus and control solutions.

Surfaces for the liquid crystal cell are prepared as follows. Fisher's Finest, premium grade glass slides (Fisher Scientific Inc., Pittsburgh, Pa.) are used to prepare the optical cells to record the textures of the DSCG in the presence of VSV particles with anti-VSV antibodies. Obliquely deposited gold films are prepared by the deposition of the gold at a fixed angle of incidence of 30°-60° (measured from the normal to the surface) in an electron beam evaporator. A layer of titanium is used to promote adhesion between the glass slide and the film of gold. Monolayers are formed on the surfaces of gold films by immersion of the films in ethanolic solutions containing 1-2 mM of $HS(CH_2)_{11}(OCH_2CH_2)_qOH$. After 24 hours of immersion at room temperature, the slides are removed from the solution and rinsed with ethanol and dried under nitrogen.

The next step involves mixing anti-VSV antibody (Ab) with VSV or control cell lysate in liquid crystal. Concentrations of VSV between 107 to 108 pfu/mL of virus particles in solution causes the non-uniform alignment of DSCG. When the virus concentration is reduced to less than 107 pfu/mL, the mesomorphic phases of DSCG liquid crystals resume their uniform alignment. Therefore, a starting concentration of VSV is set at 106 pfu/mL, which will not disturb the uniform alignment of DSCG adding anti-VSV antibodies to the solution causes the optical appearance of the DSCG to become non-uniform whereas for the control cell lysate samples, addition of anti-VSV antibody does not alter the uniform alignment of the DSCG liquid crystals.

An optical cell is fabricated by pairing a PEG monolayer surface with an octyltrichlorosilane (OTS)-treated glass slide. The two surfaces are spaced apart using 13 μm thick Saran wrap to allow LC to be introduced into the LC cell. To make OTS-treated glass slides, glass slides cleaned with piranha solution are immersed in a 10 mM solution of octyltrichlorosilane in n-heptane for 30 minutes at room temperature, rinsed with methylene chloride, and dried under a stream of nitrogen.

The optical cells are filled with the VSV/anti-VSV antibody/DSCG solution or the control cell lysate/anti-VSV antibody/DSCG solution as follows. Briefly, in separate tubes, 2 μL of VSV (5×107 pfu/mL) or cell lysate with equal amount of total protein is added to 8 μL of anti-VSV antibodies (0.1 mg to 1 mg/ml) and 40 μL of 15% (w/w) DSCG, then a drop of lyotropic liquid crystal either containing control cell lysate or VSV is applied to the center of the Saran wrap. The second SAM is placed on top of the lyotropic liquid crystal, and the saran wrap and the two SAMs are clipped together by two binder clips. The directions of deposition of the gold in the two gold films are parallel. The optical image of the lyotropic liquid crystal in the cell is observed with an Olympus BX-60 polarizing light microscope (Tokyo, Japan) in transmission mode.

With the concentration of VSV at 106 pfu/mL in DSCG, the solution gives a uniform appearance under the polarizing light scope, and as the anti-VSV antibody concentration of the solution is increased, VSV will be bound and bridged by antibodies and form lattice structure because the antibody is bivalent in its reactions with antigen and has the capacity to crosslink antigens. The appearance of the control cell lysate exhibits a similar optical appearance with or without the addition of anti-VSV antibodies in DSCG solutions.

Another class of non-amphiphilic liquid crystal is shown below. In this system, when $R^1$=$R^2COO^-$, the liquid crystal forms mesophases in water.

R1, R2 = [structures showing: carboxylate with Na+; trimethylammonium; sulfonate SO3−; sulfate OSO3−; and polyether chain with n = 1 to 5, R = H or CH3]

Protocols and Tests for Investigating the Effect of Liquid Crystals on Cells In this example, tests were carried out to determine whether a particular virus, vesicular stomatitis virus (VSV) could be incubated with liquid crystals and still retain its ability to infect its host cells, in this case HeLa cells. These investigations were carried out in three discrete stages.

The virus used in these studies was vesicular stomatitis virus (VSV) in STE buffer. The virus was purified from an infected cell culture. VSV is an important pathogenic virus for cattles and causes fever and vesicles in the mouth and on the feet. Negatively stained virions show that this virus is bullet-shaped like the rabies virus.

1. Evaluation of the Effects of Liquid Crystals on HeLa Cells

HeLa mammalian cell line (from human cervical cancer cells) were grown in poly-L-lysine (MW 30,000 to 70,000)-treated coverslips in a 12-well plate in MEM medium supplemented with 10% fetal bovine serum. HeLa cells were grown in tissue culture plates until the cells reached a confluency of 90 to 95% within 24 hrs and were maintained at 37° C. with 5% $CO_2$.

After incubation for less than one day, the DMEM was removed, the cells washed with PBS, 250 µl of the liquid crystal solution was overlaid. The following liquid crystal solutions were tested.

A) 7% (w/v) DSCG in DMEM cell culture medium
B) 7% (w/v) DSCG in $H_2O$
C) 15% (w/v) DSCG in $H_2O$
D) 30% (w/v) $A_3$ in $H_2O$
E) 21% (w/v) $C_{14}AO$ in $H_2O$ (with 3% $C_{10}OH$)

The overlaid cultures were incubated at 37° C. for 4 hours, at which time the liquid crystals were removed, the cells were washed with PBS, and 1 mL of medium DMEM was added back to the cells. The cells were then incubated in the medium at 37° C. for an additional 4 days and then evaluated for morphology and viability. See FIGS. 11A-11F, 12A-12F, and 13A-13F.

2. Effect of Liquid Crystal on Cells Inoculated with Virus

The second stage in evaluating the biocompatibility of the liquid crystals on VSV was to determine whether cells exposed to the liquid crystal are infected by a viral inoculum.

Figure 14:
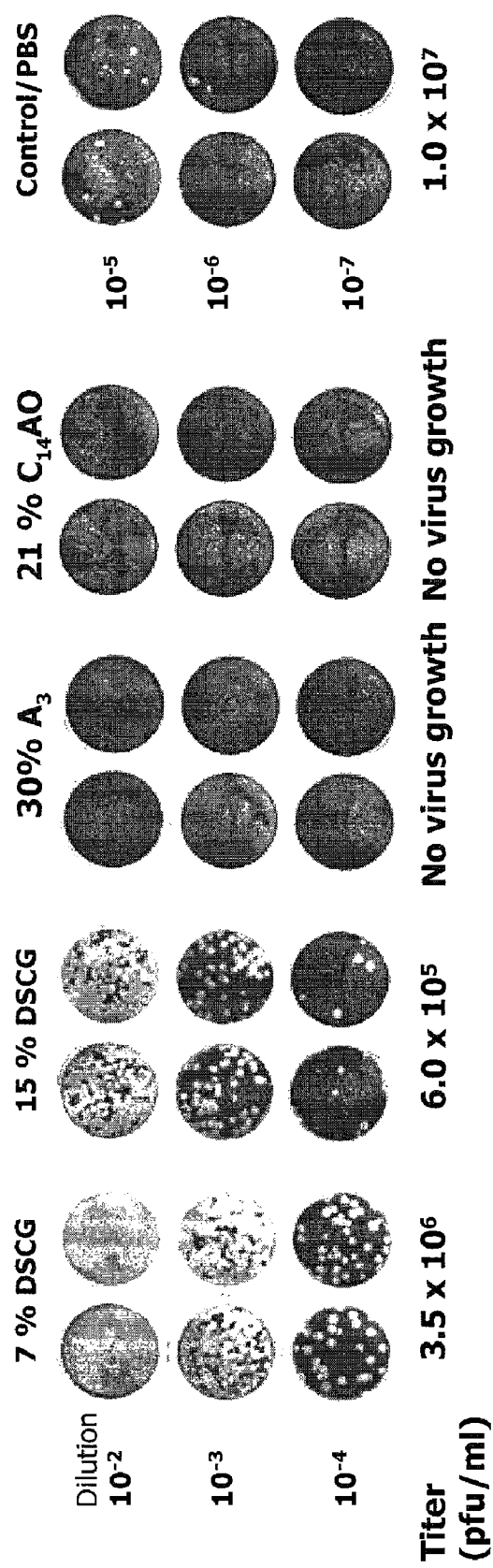
FIG. 14 is a scanned image showing the effect of various liquid crystals when vesicular stomatitis virus (VSV) is inoculated to cells HeLa cells. These cells shows the VSV infection of HeLa cells after contact with the liquid crystal for 1 hour (virus titration of supernatant at 2 days after growing in medium).

In this experiment, HeLa cells were incubated as described above and overlaid with the liquid crystal solutions A-E as described above to which $1.5 \times 10^7$ pfu of VSV was added. The cells were incubated for 1 hour at 37° C. in the presence of the liquid crystal/VSV mixture. The inoculum and liquid crystal were then removed, the cells washed with PBS as described above, overlaid with fresh DMEM, and incubated at 37° C. for 2 days, at which time the supernatant was collected from each well and cell debris was removed by centrifugation before subjected to virus titration. The supernatant was then titrated onto tissue culture plates supporting a confluent growth of HeLa cells and the plates were incubated at 37° C. for 24-48 hours before staining the cells with a crystal violet/formaldehyde/ethanol. The results are presented in FIG. 14 and indicate that VSV can infect cells in the presence of DSCG. However, no growth of VSV was observed in the presence of either $A_3$ or $C_{14}AO$.

3. Effect of Liquid Crystal on VSV Infectivity.

A further aspect of the investigation of the effect of liquid crystal on the ability of VSV to infect cells is to evaluate the effect of the liquid crystal on the virus itself, i.e. without considering the effect of the liquid crystal on the cells.

Aliquots of $2 \times 10^7$ plaque forming units (pfu) of VSV in 10 µl was incubated with 90 µl of liquid crystal solutions A-E at room temperature for 30 minutes, 1 hour, or 4 hours, 400 µl of medium DMEM was then added to these inocula, and the mixtures were stored at −80° C. until titration was carried out on HeLa cells about 2 days later. These inocula were then tested by titrating them in HeLa cells in serial dilutions as indicated in the schematic. The results are presented in FIG. 21 and indicate that VSV is stable in the presence of DSCG, even after a 4 hour incubation with the liquid crystal. However, no growth of VSV was observed from the inocula incubated with $A_3$ or $C_{14}AO$.

Various protocols were used to investigate the effect of various liquid crystals on cells and viruses as described above. These protocols are summarized in the schematic illustrations of FIGS. 17-21.

When DSCG in water is used (pH<6), the mixture appeared too acidic for the cells. Alternatively, the DSCG may out-compete the binding of the cells to the poly-L-lysine on the surface. Either way, cells rounded up and detached from the surface during incubation with the DSCG in water. However, cells that survived the DSCG in water treatment, proliferated well after the medium was added.

The liquid crystal $A_3$ affected cells in a different way because the cell membranes started to show a rough appearance (blebbing) and the nuclei condensed (darken in color) after 30 minutes.

The effect of $C_{14}AO$ in $H_2O$ (with 3% $C_{10}OH$) on the cells was almost instantaneous such that 5 minutes after addition of reagent, the cells were stressed. The cells exhibited doughnut ring appearance inside the cells up until 2 days post treatment, and then giant cells were formed. It is speculated that this liquid crystal may have affected the cell membrane which are fused to form the multi-nuclei giant cells.

The experimental results show that VSV can infect cells in the presence of liquid crystals such as DSCG. Even though cells were stressed during the inoculation (possible due to the acidity of the solution), once the cells were washed and the culture medium was replaced, the cells recovered and were able to support the growth of virus. VSV was found to be stable in the presence of DSCG. For example, even after 4 hours incubation in DSCG at room temperature, the virus retained its ability to infect cells and the concentration of the virus had not changed significantly.

In the presence of $A_3$ (30% (w/v) in $H_2O$) or $C_{14}AO$ in $H_2O$ (21% (w/v) with 3% $C_{10}OH$), no growth of VSV was observed. This effect may be due to the toxicity of the liquid crystal with respect to the cells or may be due to inhibition of the virus by the liquid crystal.

All references cited in this document including patents, published patent applications, international patent applications, non-patent literature documents, information available on the internet, and other such information are herein incorporated by reference in their entirety and for all purposes as if fully set forth herein.

It is understood that the invention is not limited to the embodiments set forth herein for illustration, but embraces all such forms thereof as come within the scope of the claims.

What is claimed is:

1. A liquid crystal cell culture media, comprising at least one liquid crystal compound and at least one cell culture component selected from a vitamin, an amino acid, a sugar, or combinations thereof, wherein the at least one liquid crystal comprises a compound comprising a fluorinated phenyl group, a fluorinated cyclohexyl group; a cholesteric liquid crystal, or a liquid crystal that exhibits reduced toxicity towards cells.

2. The liquid crystal cell culture media of claim 1, wherein the cell culture media comprises at least three amino acids selected from L-alanine, L-arginine, L-asparagine, L-aspartic acid, L-cystine, L-glutamic acid, L-glutamine, glycine, L-histidine, hydroxy-L-proline, L-isoleucine, L-leucine, L-lysine, L-methionine, L-ornithine, L-phenylalanine, L-proline, L-serine, L-taurine, L-threonine, L-tryptophan, L-tyrosine, L-valine, or salts or combinations thereof.

3. The liquid crystal cell culture media of claim 1, wherein the cell culture media comprises at least five amino acids selected from L-alanine, L-arginine, L-asparagine, L-aspartic acid, L-cystine, L-glutamic acid, L-glutamine, glycine, L-histidine, hydroxy-L-proline, L-isoleucine, L-leucine, L-lysine, L-methionine, L-ornithine, L-phenylalanine, L-proline, L-serine, L-taurine, L-threonine, L-tryptophan, L-tyrosine, L-valine, or salts or combinations thereof.

4. The liquid crystal cell culture media of claim 1, wherein the cell culture media comprises at least eight amino acids selected from L-alanine, L-arginine, L-asparagine, L-aspartic acid, L-cystine, L-glutamic acid, L-glutamine, glycine, L-histidine, hydroxy-L-proline, L-isoleucine, L-leucine, L-lysine, L-methionine, L-ornithine, L-phenylalanine, L-proline, L-serine, L-taurine, L-threonine, L-tryptophan, L-tyrosine, L-valine, or salts or combinations thereof.

5. The liquid crystal cell culture media of claim 1, wherein the cell culture media further comprises at least two salts selected from $CaCl_2$, NaCl, $NaHCO_3$, $Na_2HPO_4$, $NaH_2PO_4$, KCl, $K_2HPO_4$, $KH_2PO_4$, $MgSO_4$, $MgCl_2$, $Fe(NO_3)_3$, $FeSO_4$, $CuSO_4$, $ZnSO_4$, $ZnCl_2$, $CoCl_2$, $CuCl_2$, $MnCl_2$, $(NH_4)_2MoO_4$, or hydrates or combinations thereof.

6. The liquid crystal cell culture media of claim 1, wherein the cell culture media comprises at least two vitamins selected from ascorbic acid, D-biotin, choline, choline chloride, choline bitartrate, folic acid, myo-inositol, inositol, niacin, niacinamide, nicotinamide, p-aminobenzoic acid, D-pantothenic acid, pyridoxine, pyridoxal, riboflavin, DL-thioctic acid, thiamine, vitamin B12, vitamin A alcohol, vitamin D-2, vitamin E, menadione, nicotinic acid, alpha-tocopherol, or salts or combinations thereof.

7. The liquid crystal cell culture media of claim 1, wherein the cell culture media comprises at least five vitamins selected from ascorbic acid, D-biotin, choline, choline chloride, choline bitartrate, folic acid, myo-inositol, inositol, niacin, niacinamide, nicotinamide, p-aminobenzoic acid, D-pantothenic acid, pyridoxine, pyridoxal, riboflavin, DL-thioctic acid, thiamine, vitamin B12, vitamin A alcohol, vitamin D-2, vitamin E, menadione, nicotinic acid, alpha-tocopherol, or salts or combinations thereof.

8. The liquid crystal cell culture media of claim 1, wherein the cell culture media comprises at least eight vitamins selected from ascorbic acid, D-biotin, choline, choline chloride, choline bitartrate, folic acid, myo-inositol, inositol, niacin, niacinamide, nicotinamide, p-aminobenzoic acid, D-pantothenic acid, pyridoxine, pyridoxal, riboflavin, DL-thioctic acid, thiamine, vitamin B12, vitamin A alcohol, vitamin D-2, vitamin E, menadione, nicotinic acid, alpha-tocopherol, or salts or combinations thereof.

9. The liquid crystal cell culture media of claim 1, wherein the at least one liquid crystal is a cholesteric liquid crystal.

10. The liquid crystal cell culture media of claim 1, wherein the at least one liquid crystal comprises a fluorinated cyclohexyl group.

11. The liquid crystal cell culture media of claim 1, wherein the at least one liquid crystal comprises a fluorinated phenyl group.

12. The liquid crystal cell culture media of claim 1, wherein the at least one liquid crystal comprises a difluorinated phenyl group.

13. The liquid crystal cell culture media of claim 1, wherein the at least one liquid crystal comprises a difluorinated compound having the following formula where Z is an alkyl group having 1, 2, 3, 4, 5, 6, 7, 8, 9, 10, 11, 12, 13, 14, 15, or 16 carbon atoms

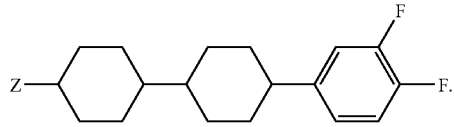

14. The liquid crystal cell culture media of claim 1, wherein the at least one liquid crystal exhibits lyotropic or a thermotropic properties.

15. The liquid crystal cell culture media of claim 1, wherein the liquid crystal cell culture media comprises 2 or more different liquid crystals.

16. The liquid crystal cell culture media of claim 1, further comprising water.

17. The liquid crystal cell culture media of claim 1, wherein the at least one cell culture component comprises glucose.

* * * * *